United States Patent
Gillies et al.

(10) Patent No.: US 9,940,709 B2
(45) Date of Patent: Apr. 10, 2018

(54) SYSTEMS AND METHODS FOR DIAGNOSING TUMORS IN A SUBJECT BY PERFORMING A QUANTITATIVE ANALYSIS OF TEXTURE-BASED FEATURES OF A TUMOR OBJECT IN A RADIOLOGICAL IMAGE

(71) Applicants: H. LEE MOFFITT CANCER CENTER AND RESEARCH INSTITUTE, INC., Tampa, FL (US); UNIVERSITY OF SOUTH FLORIDA, Tampa, FL (US)

(72) Inventors: Robert J. Gillies, Tampa, FL (US); Lawrence O. Hall, Tampa, FL (US); Dmitry B. Goldgof, Lutz, FL (US)

(73) Assignees: H. LEE MOFFITT CANCER CENTER AND RESEARCH INSTITUTE, INC., Tampa, FL (US); UNIVERSITY OF SOUTH FLORIDA, Tampa, FL (US)

( * ) Notice: Subject to any disclaimer, the term of this patent is extended or adjusted under 35 U.S.C. 154(b) by 3 days.

(21) Appl. No.: 15/028,857

(22) PCT Filed: Oct. 10, 2014

(86) PCT No.: PCT/US2014/060076
§ 371 (c)(1),
(2) Date: Apr. 12, 2016

(87) PCT Pub. No.: WO2015/054597
PCT Pub. Date: Apr. 16, 2015

(65) Prior Publication Data
US 2016/0260211 A1 Sep. 8, 2016

Related U.S. Application Data

(60) Provisional application No. 61/890,217, filed on Oct. 12, 2013.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/055* (2013.01); *A61B 6/03* (2013.01); *A61B 6/032* (2013.01);
(Continued)

(58) Field of Classification Search
CPC ................ G06T 7/00; A61B 5/00; A61B 6/00
(Continued)

(56) References Cited

U.S. PATENT DOCUMENTS 6,858,007 B1 * 2/2005 Akselrod .................. G06T 7/12
128/916
8,014,576 B2 * 9/2011 Collins .................... A61B 8/08
382/128

(Continued)

OTHER PUBLICATIONS

Balagurunathan, Y., et al., "Reproducibility and prognosis of quantitative features extracted from CT images," Translational Oncology, vol. 7, No. 1, 2014, pp. 72-87.
(Continued)

*Primary Examiner* — Abolfazl Tabatabai
(74) *Attorney, Agent, or Firm* — Meunier Carlin & Curfman LLC

(57) ABSTRACT

An example method for diagnosing tumors in a subject by performing a quantitative analysis of a radiological image can include identifying a region of interest (ROI) in the radiological image, segmenting the ROI from the radiological image, identifying a tumor object in the segmented ROI and segmenting the tumor object from the segmented ROI. The method can also include extracting a plurality of quantitative features describing the segmented tumor object, and
(Continued)

classifying the tumor object based on the extracted quantitative features. The quantitative features can include one or more texture-based features.

22 Claims, 10 Drawing Sheets

(51) Int. Cl.
*A61B 6/03* (2006.01)
*A61B 5/055* (2006.01)
*G06T 7/41* (2017.01)
*A61B 5/00* (2006.01)
*A61B 6/00* (2006.01)

(52) U.S. Cl.
CPC ............... *A61B 6/037* (2013.01); *A61B 6/50* (2013.01); *A61B 6/5217* (2013.01); *G06T 7/41* (2017.01); *A61B 6/469* (2013.01); *G06T 2207/10081* (2013.01); *G06T 2207/30061* (2013.01); *G06T 2207/30096* (2013.01)

(58) Field of Classification Search
USPC ....... 382/128, 129, 130, 131, 132, 133, 134; 378/21, 23, 28, 41, 901; 600/300, 425, 600/427, 532
See application file for complete search history.

(56) References Cited

U.S. PATENT DOCUMENTS 8,300,938 B2 * 10/2012 Can ..................... G06K 9/0014
   382/128
9,721,340 B2 * 8/2017 Gillies ................ A61B 5/7271

OTHER PUBLICATIONS

Balagurunathan, Y., et al., "Test-Retest Reproducibility Analysis of Lung CT Image Features," J Digit Imaging, vol. 27, 2014, pp. 805-823.
Krewer, H., et al., "Effect of Texture Features in Computer Aided Diagnosis of Pulmonary Nodules in Low-Dose Computed Tomography," IEEE International Conference on Systems, Man, and Cybernetics, 2013, 5 pages.
International Preliminary Report on Patentability and Written Opinion, dated Apr. 12, 2016, received in connection with corresponding International Patent Application No. PCT/US2014/060076.

* cited by examiner

SYSTEMS AND METHODS FOR DIAGNOSING TUMORS IN A SUBJECT BY PERFORMING A QUANTITATIVE ANALYSIS OF TEXTURE-BASED FEATURES OF A TUMOR OBJECT IN A RADIOLOGICAL IMAGE

CROSS-REFERENCE TO RELATED APPLICATIONS

This application is a national stage application under 35 U.S.C. 371 based on application PCT/US2014/060076, which claims the benefit of and priority to U.S. Provisional Application No. 61/890,217, filed on Oct. 12, 2013, the disclosures of which are expressly incorporated herein by reference in their entirety.

STATEMENT REGARDING FEDERALLY FUNDED RESEARCH

This invention was made with Government support under Grant No. CA143062 awarded by the National Institutes of Health. The Government has certain rights in the invention.

BACKGROUND

Lung cancer is responsible for the greatest number of cancer related deaths in the United States. The primary precursor to lung cancer is the development of pulmonary nodules. Several diagnostic procedures are available to detect these nodules including pulmonary function tests, blood tests, biopsy, and imaging tests such as X-ray, magnetic resonance imaging (MRI), computed tomography (CT), and positron emission tomography (PET). Regardless of the diagnostic procedure used, the ultimate diagnosis is usually confirmed by completing a biopsy.

The advent of low-dose helical computed tomography has made it possible to provide relatively low risk screening for high risk patients. Though still somewhat controversial, results of the National Lung Screening Trial (NLST) have shown a 20% decrease in mortality with the use of low-dose CT compared to X-ray findings. The sensitivity of the procedure is its bane; many of the detected nodules are not cancerous.

Accurate classification (or prediction) of pulmonary nodules to be cancerous is key to determining further diagnosis and treatment options. In order to provide medical personnel with the information to accurately determine the nature of the nodule, several computer aided diagnosis systems have been created to classify pulmonary nodules. Traditionally, these systems have been based on size and volume measurements.

SUMMARY

An example method for diagnosing tumors in a subject by performing a quantitative analysis of a radiological image can include identifying a region of interest (ROI) in the radiological image, segmenting the ROI from the radiological image, identifying a tumor object in the segmented ROI and segmenting the tumor object from the segmented ROI. The method can also include extracting a plurality of quantitative features describing the segmented tumor object, and classifying the tumor object based on the extracted quantitative features. The quantitative features can include one or more texture-based features with or without size and shape features.

Optionally, predicting/classifying the indeterminate pulmonary nodule to become tumor/malignant or benign may be based on the extracted quantitative features. Further, the tumor object may be either a nodule or a mass that comprises of all anomalies, including ground-glass opacity (GGO) nodules. Predicting/classifying patient tumor (lesions) prognosis/relapse or progression may be based on extracted quantitative features. The tumor object may include all types of abnormalities including, but not limited to, ground glass opacities (GGO), histology and staging. The prediction/classification could be for a sunset of histology and staging (based on TNM scale). Alternatively or additionally, the tumor object can be classified using a decision tree algorithm, a nearest neighbor algorithm or a support vector machine. It should be understood that these classification algorithms are provided only as examples and that other known classification algorithms can be used.

Alternatively or additionally, each of the texture-based features describes a spatial arrangement of image intensities within the tumor object. For example, the texture-based features can include a run-length texture feature, a co-occurrence texture feature, a Laws texture feature, a wavelet texture feature, gray level (Hounsfield scale) histogram texture feature. Additionally, the quantitative features can optionally include one or more shape-based features. Each of the shape-based features can describe a location, quantification of extend of attachment to the lung wall (circumference of tumor to attachment extent), a geometric shape, a volume, a surface area, a surface-area-to-volume ratio or a compactness of the tumor object.

The ROI can optionally be a lung field. It should be understood that a lung field is provided only as an example. This disclosure contemplates that the ROI can be a region in another organ of the subject. Optionally, the radiological image is a low-dose computed tomography (CT) image. Although a low-dose CT image is provided as an example, this disclosure contemplates that the radiological image can be another type of image, including but not limited to, an X-ray image, an MRI and a PET image.

Optionally, the method can further include reducing the extracted quantitative features to a subset of extracted quantitative features, and classifying the tumor object based on the subset of extracted quantitative features. For example, the subset of extracted quantitative features can optionally include one or more quantitative features that are predictive of being a tumor. Accordingly, the method can optionally include determining the one or more quantitative features that are predictive of the classification of the tumor object using at least one of a Recursive Elimination of Features (Relief-F) algorithm, a Correlation-Based Feature Subset Selection for Machine Learning (CFS) algorithm or a Relief-F with Correlation Detection algorithm or iterative search.

Alternatively or additionally, the subset of extracted quantitative features can optionally include one or more non-redundant quantitative features having adequate reproducibility and dynamic range. For example, to reduce the extracted quantitative features to a subset of extracted quantitative features, the method can optionally include eliminating one or more of the extracted quantitative features which are not part of reproducible features based on test retest repeatable study where baseline radiological image and a subsequent radiological image less than a predetermined reproducibility value. The subsequent radiological image is an image captured a fixed period of time after the baseline radiological image was captured. The reproducibility metric is a concordance correlation coefficient (CCC) or Interclass correlation coefficient (ICC). This disclosure contemplates using other known metrics for the reproducibility of a feature between baseline and subsequent images. Optionally, the predetermined reproducibility value is less than 0.90. Although 0.90 is provided as an example of the predetermined reproducibility value, it should be understood that values more or less than 0.90 can be used.

Alternatively or additionally, to reduce the extracted quantitative features to a subset of extracted quantitative features, the method can optionally include eliminating one or more of the extracted quantitative features having a dynamic range less than a predetermined dynamic range value. Optionally, the predetermined dynamic range value is greater than 0.55 (e.g., 55% of its dynamic range). Although 0.55 is provided as an example of the predetermined dynamic range value, it should be understood that values more or less than 0.55 can be used.

Alternatively or additionally, to reduce the extracted quantitative features to a subset of extracted quantitative features, the method can optionally include eliminating one or more of the extracted quantitative features that are redundant quantitative features. For example, the method can include calculating a coefficient of determination ($R^2_{Bet}$) between a pair of (least two) quantitative features. Accordingly, one or more quantitative features having an $R^2_{Bet}$ greater than a predetermined redundancy value can be eliminated It should be understood that these eliminated quantitative features are highly correlated and are considered redundant quantitative features. Optionally, the predetermined redundancy value is greater than 0.95. Although 0.95 is provided as an example of the predetermined redundancy value, it should be understood that values more or less from 0.75 to 0.99 are relevant, appropriate levels can be used.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for diagnosing tumors in a subject by performing a quantitative analysis of a low-dose CT image, it will become evident to those skilled in the art that the implementations are not limited thereto, but are applicable for diagnosing tumors in a subject by performing a quantitative analysis of other types of radiological images.

Low-dose helical computed tomography (LDCT) has facilitated the early detection of lung cancer through pulmonary screening of patients. There have been a few attempts to develop a computer-aided diagnosis system for classifying pulmonary nodules using size and shape, with little attention to texture features. As described herein, texture and shape features were extracted from pulmonary nodules selected from the Lung Image Database Consortium (LIDC) data set. Several classifiers including Decision Trees, Nearest Neighbor, linear discriminant and Support Vector Machines (SVM) were used for classifying malignant and benign pulmonary nodules. An accuracy of 90.91% was achieved using a 5-nearest-neighbors algorithm and a data set containing texture features only. Laws and Wavelet features received the highest rank when using feature selection implying a larger contribution in the classification process. Considering the improvement in classification accuracy, it is possible to perform computer-aided diagnosis of pulmonary nodules in LDCT by performing a quantitative analysis of texture features.

Figure 1:
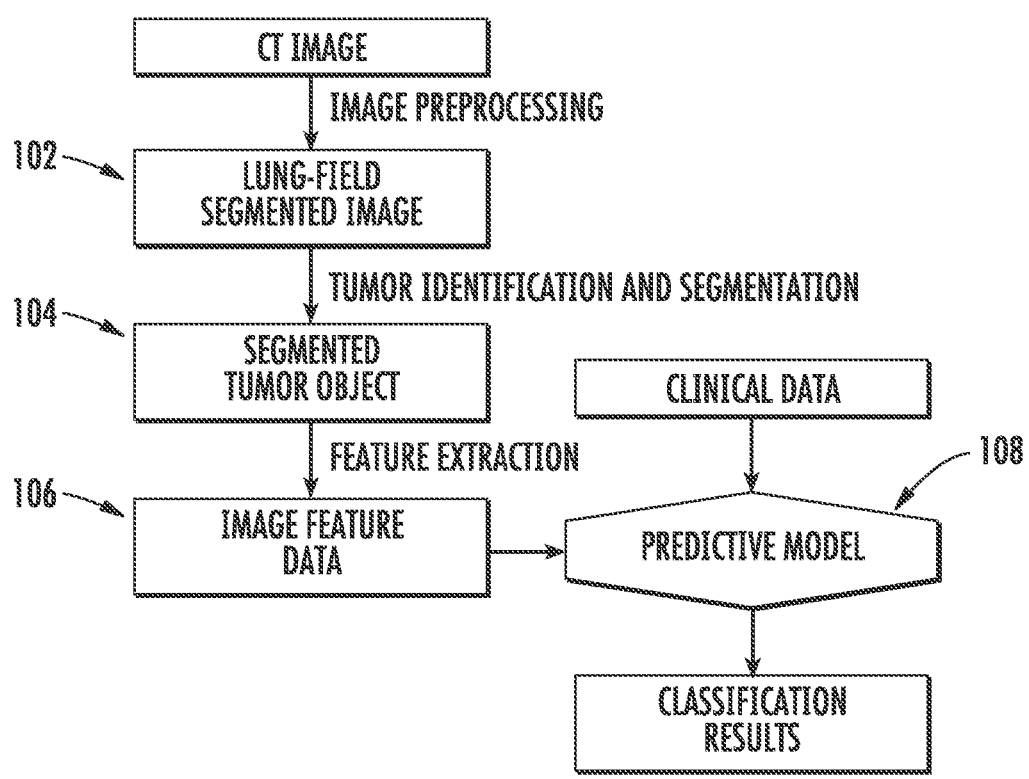
FIG. 1 is a flow diagram illustrating example operations for diagnosing tumors in a subject by performing a quantitative analysis of a radiological image as described herein.
Figure 2:
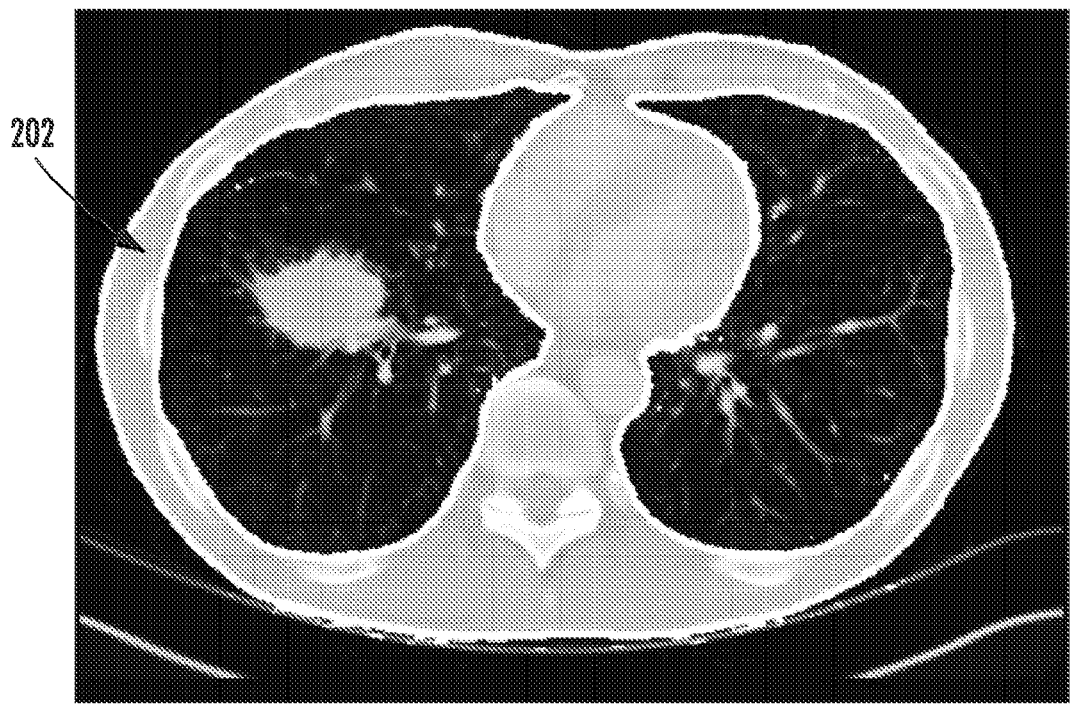
FIG. 2 is an example segmented ROI in a radiological image.

Referring now to FIG. 1, a flow diagram illustrating example operations for diagnosing tumors in a subject by performing a quantitative analysis of a radiological image is shown. In the examples below, the radiological image is a low-dose computed tomography (CT) image. Although a low-dose CT image is provided as an example, this disclosure contemplates that the radiological image can be another type of image, including but not limited to, an X-ray image, an MRI and a PET image. At 102, a region of interest (ROI) in the radiological image is identified and then segmented from the radiological image. An example segmented ROI 202 in a radiological image is shown in FIG. 2. In particular, the segmented ROI 202 is a segmented lung field in FIG. 2.

Figure 3:
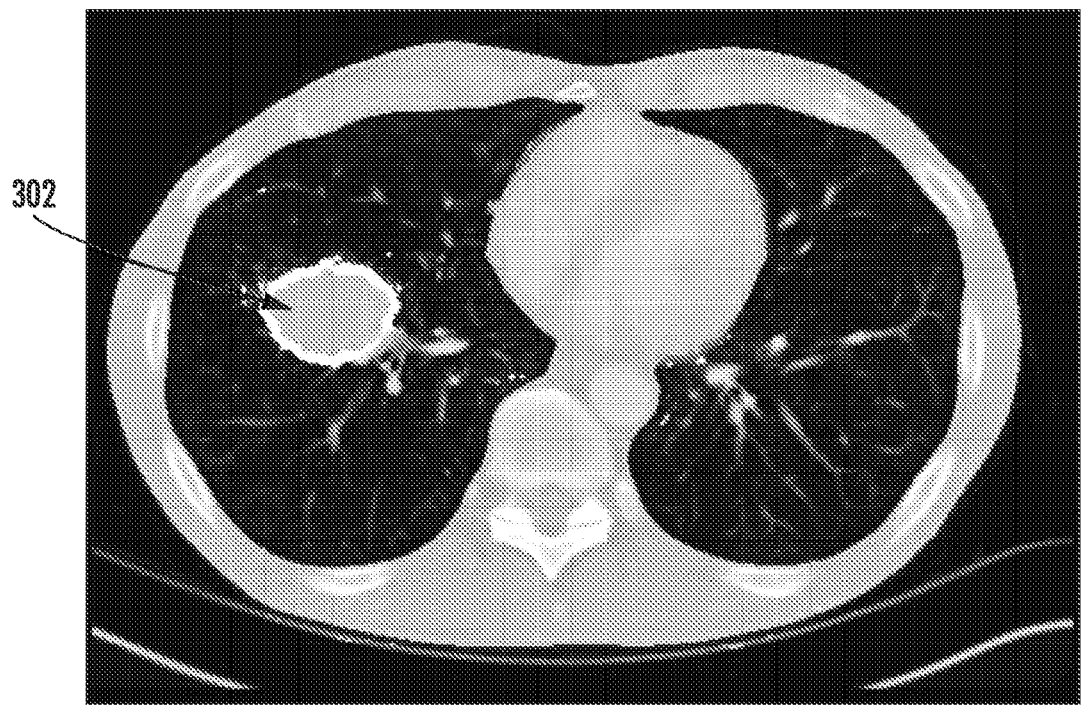
FIG. 3 is an example segmented object in a radiological image.

It should be understood that the ROI can be a region in another organ of the subject and that a lung field is provided only as an example. At 104, a tumor object is identified in the segmented ROI and then segmented from the radiological image. An example segmented tumor object 302 in a radiological image is shown in FIG. 3. In particular, the segmented tumor object 302 is a segmented pulmonary nodule in FIG. 3. Segmenting is a well-known technique in image processing, and this disclosure contemplates using any manual, semi-automatic and/or automatic algorithm to segment the ROI and/or the tumor object from the radiological image. For example, the ROI and/or the tumor object can be segmented using a region growing algorithm.

At 108, a plurality of quantitative features describing the segmented tumor object can be extracted. The quantitative features can include one or more texture-based features. As used herein, the texture-based features describe a spatial arrangement of image intensities within the tumor object. For example, the texture-based features can include a run-length texture feature, a co-occurrence texture feature, a Laws texture feature, a wavelet texture feature or a histogram texture feature. Each of these texture-based features is described in further detail below. Additionally, Tables A1 and A2 below provide a description of various quantitative features used to describe tumor objects. In some implementations, a total number of quantitative features is optionally greater than approximately 200. Additionally, a number of texture-based features is optionally greater than approximately 150. Although 219 quantitative features are included in Table A2, it should be understood that more or less than 219 quantitative features can be extracted from the tumor object. In addition, about 119 features were obtained on a single central slice referred as 2D features. The quantitative features provided in Table A2 are provided as examples only (for 3D).

Run-length texture features examine runs of similar gray values in an image. Runs may be labeled according to their length, gray value, and direction (either horizontal or vertical). Long runs of the same gray value correspond to coarser textures, whereas shorter runs correspond to finer textures. Texture information can be quantified by computing 11 features derived from the run-length distribution matrix. These 11 feature are: 1: Short Run Emphasis (SRE). 2: Long Run Emphasis (LRE). 3: Gray-Level Non-uniformity (GLN). 4: Run Length Non-uniformity (RLN). 5: Run Percentage (RP). 6: Low Gray-Level Run Emphasis (LGRE). 7: High Gray-Level Run Emphasis (HGRE). 8: Short Run Low Gray-Level Emphasis (SRLGE). 9: Short Run High Gray-Level Emphasis (SRHGE). 10: Long Run Low Gray-Level Emphasis (LRLGE). 11: Long Run High Gray-Level Emphasis (LGHGE).

Co-occurrence texture features are obtained from the co-occurrence matrix, which is a matrix that contains the frequency of one gray level intensity appearing in a specified spatial linear relationship with another gray level intensity within a certain range. Computation of features requires first constructing the co-occurrence matrix, then different measurements can be calculated based on the matrix. The different measurements include: contrast, energy, homogeneity, entropy, mean and max probability.

Run-length & Co-occurrence features may find some correlation to radiologist visualized texture. The run length is defined as a measure of contiguous gray levels along a specific orientation. Fine textures tend to have short run length while coarser texture will have longer run lengths with similar gray level. These features capture coarseness in 3D image structure and have been found useful in a number of texture analyses [20,21]. If R (k,p) is the run length matrix $n_1$ by $n_2$, at gray level k then the number of such lengths equals p, along an orientation, in the volume (x,y,z). One useful measure of run length in this study has been the measure of Non-uniformity ($RunL_{GLN}$) which measures extent of smoothness or similarity in the image.

$$RunL_{GLN} = \left( 1/n \sum_{k=1}^{n_1} \left( \sum_{p=1}^{n_2} R(k, p) \right)^2 \right)$$

The co-occurrence matrices and run-length features can be obtained in 3D, the features are calculated in 13 different directions, with each direction, processing is done by plane instead of slice. Hence, information between slices is not ignored.

Laws features were constructed from a set of five one-dimensional filters, each designed to reflect a different type of structure in the image. These one-dimensional filters are defined as E5 (edges), S5 (spots), R5 (ripples), W5 (waves), and L5 (low pass, or average gray value). By using these 1-D convolution filters, 2-D filters are generated by convolving pairs of these filters, such as L5L5, E5L5, S5L5, W5L5, R5L5, etc. In total, it is possible to generate 25 different 2-D filters. 3D laws filters were constructed similarly to 2D. 3D filters are generated by convolving 3 types of 1D filter, such as L5L5L5, L5L5E5, L5L5S5, L5L5R5, L5L5W5, etc. The total number of 3-D filters is 125. For the 3D case, after the convolution with the 3D filters for the image, the energy of the texture feature can be computed by the following equation:

$$\text{Energy} = \frac{1}{R} \sum_{i=N+1}^{I-N} \sum_{j=N+1}^{J-N} \sum_{k=N+1}^{K-N} h^2(i, j, k),$$

where R is a normalizing factor, I and J, K are image dimensions, h(i,j,k) is derived from the convolution filters and original image. For the 2D case, the above equation is very similar, but without the 3rd (e.g., z-direction) dimension.

Wavelet texture features are obtained using the discrete wavelet transform, which can iteratively decompose an image (2D) into four components. Each iteration involves convolving the image with wavelet kernel both horizontally and vertically, followed by down sampling to obtain low-frequency (low pass) and high-frequency (high pass) components. Thus, doing it in both the directions four components are generated: a high-pass/high-pass component consisting of mostly diagonal structure, a high-pass/low-pass component consisting mostly of vertical structures, a low-pass/high-pass component consisting mostly of horizontal structure, and a low-pass/low-pass component that represents a blurred version of the original image. Subsequent iterations then repeat the decomposition on the low-pass/low-pass component from the previous iteration. These subsequent iterations highlight broader diagonal, vertical, and horizontal textures. And for each component, the energy (referred to with a suffix P1) & entropy (referred to with a suffix P2) of a feature is calculated. A wavelet transform of a 3D signal can be achieved by applying the 1D wavelet transform along all the three directions (x,y,z). Featured obtained in each level of decomposition is referred with suffix L (example: L1, L2) and level of decomposition is referred to with a prefix C (example: C1 to C9).

Histogram texture features are obtained using the intensity histogram, h(a), which is the number of pixels that occurred for brightness level "a" plotted against their brightness level (in CT based, it is Hounsfield units). The probability distribution of the brightness, P(a), can be calculated as well. Six features (e.g., mean, standard deviation, skewness, kurtosis, energy, and entropy) were then incorporated.

Alternatively or additionally, the quantitative features can optionally include one or more shape-based features. In other words, the quantitative features can include a combination of texture-based and shape-based features. The shape-based features can describe a location, a geometric shape, a volume, a surface area, a surface-area-to-volume ratio or a compactness of the tumor object. Example shape-based features are also provided in Table A2.

TABLE A1

Quantitative Feature Categories

| Category | Description | Number of Descriptors |
|---|---|---|
| C1: Tumor Size | Size, volume descriptors | 13 |
| C2: Tumor Shape (Roundness) | Roundness/circularity descriptors | 12 |
| C3: Tumor Location | Relative to pleural wall, boarder flags | 14 |
| C4: Pixel Attenuation Histogram | Statistics on the Intensity values (in HU) | 8 |
| C5: Grayscale: Runlength & CoOccurrence | Run length and Co-occurrence patterns | 17 |
| C6: Texture: Laws features | Laws Kernel (energy) | 125 |
| C7: Texture: Wavelets | Wavelet kernels (entropy and energy) | 30 |
| | Total | 219 |

TABLE A2

Description of Quantitative Feature Used to Describe Tumor Objects (e.g., a lung tumor)

| Sno | Feature Index | Description of the Features | Feature Category |
|---|---|---|---|
| 1 | F1 | Long Diameter | C1.Tumor Size |
| 2 | F2 | Short Axis-LongDiameter | |
| 3 | F3 | Short Axis | |
| 4 | F6 | Volume (cm) | |
| 5 | F33 | Area-Pixels | |
| 6 | F34 | Volume-pixels | |
| 7 | F35 | Num of Pixels | |
| 8 | F36 | Width-Pixels | |
| 9 | F37 | Thickness-Pixels | |
| 10 | F38 | Length-Pixels | |
| 11 | F39 | Length-by-Thick | |
| 12 | F40 | Length-by-Width | |
| 13 | F41 | Border-Length-Pixels | |
| 14 | F7 | 5a-3D-MacSpic | C2. Tumor Shape (Roundness) |
| 15 | F13 | 9b-3D-Circularity | |
| 16 | F14 | 9c-3D-Compact | |
| 17 | F23 | Asymmetry | |
| 18 | F24 | Compactness | |
| 19 | F25 | Density | |
| 20 | F26 | Elliptic Fit | |
| 21 | F28 | Rad-Largest-Enclosed-Ellipse | |
| 22 | F29 | Rad-Smallest-Enclosed-Ellipse | |
| 23 | F30 | Shape-Index | |
| 24 | F31 | Roundness | |
| 25 | F32 | Rectangular Fit | |
| 26 | F8 | 8a-3D-Attached to Pleural | C3.. Tumor Location |
| 27 | F9 | 8b-3D-Border-to-Lung | |
| 28 | F10 | 8c-3D-Border-to-Pleural | |
| 29 | F11 | 8d-3D-Ratio-Free-to-Attach | |
| 30 | F12 | 9a-3D-FractionalAnisotropy | |
| 31 | F15 | 9d-3D-AV-Dist-COG-to-Border | |
| 32 | F16 | 9e-3D-SD-Dist-COG-to-Border | |
| 33 | F17 | 9f-3D-Min-Dist-COG-to-Border | |
| 34 | F18 | 9g-3D-Max-Dist-COG-to-Border | |
| 35 | F19 | 10a-3D-Relative-Vol-Airspaces | |
| 36 | F20 | 10b-3D-Number-of-AirSpaces | |
| 37 | F21 | 10c-3D-Av-Vol-AirSpaces | |
| 38 | F22 | 10d-3D-SD-Vol-AirSpaces | |
| 39 | F27 | Main-Direction | |
| 40 | F4 | Mean-Hu | C4. Pixel Attenuation Histogram |
| 41 | F5 | Standard deviation-Hu | |
| 42 | F184 | Hist-Mean-L1 | |
| 43 | F185 | Hist-Standard deviation-L1 | |
| 44 | F186 | Hist-Energy-L1 | |
| 45 | F187 | Hist-Entropy-L1 | |
| 46 | F188 | Hist-Kurtosis-L1 | |
| 47 | F189 | Hist-Skewness-L1 | |
| 48 | F42 | Average CoOccurrence-Homo | C5. Runlength and |

TABLE A2-continued

Description of Quantitative Feature Used to Describe Tumor Objects (e.g., a lung tumor)

| Sno | Feature Index | Description of the Features | Feature Category |
|---|---|---|---|
| 49 | F43 | Average CoOccurrence-Mp | Cooccurrence |
| 50 | F44 | Average CoOccurrence-Constrast | |
| 51 | F45 | Average CoOccurrence-Energy | |
| 52 | F46 | Average CoOccurrence-Entropy | |
| 53 | F47 | Average CoOccurrence-Mean | |
| 54 | F48 | AvgGLN | |
| 55 | F49 | AvgHGRE | |
| 56 | F50 | AvgLGRE | |
| 57 | F51 | AvgLRE | |
| 58 | F52 | AvgLRHGE | |
| 59 | F53 | AvgLRLGE | |
| 60 | F54 | AvgRLN | |
| 61 | F55 | AvgRP | |
| 62 | F56 | AvgSRE | |
| 63 | F57 | AvgSRHGE | |
| 64 | F58 | AvgSRLGE | |
| 59 | F59 | 3D-Laws-1 (E5 E5 E5 Layer 1) | C6. Laws Texture Feature (with different convolution filters) |
| 60 | F60 | 3D-Laws-2 (E5 E5 L5 Layer 1) | |
| 61 | F61 | 3D-Laws-3 (E5 E5 R5 Layer 1) | |
| 62 | F62 | 3D-Laws-4 (E5 E5 S5 Layer 1) | |
| 63 | F63 | 3D-Laws-5 (E5 E5 W5 Layer 1) | |
| 64 | F64 | 3D-Laws-6 (E5 L5 E5 Layer 1) | |
| 65 | F65 | 3D-Laws-7 (E5 L5 L5 Layer 1) | |
| 66 | F66 | 3D-Laws-8 (E5 L5 R5 Layer 1) | |
| 67 | F67 | 3D-Laws-9 (E5 L5 S5 Layer 1) | |
| 68 | F68 | 3D-Laws-10 (E5 L5 W5 Layer 1) | |
| 69 | F69 | 3D-Laws-11 (E5 R5 E5 Layer 1) | |
| 70 | F70 | 3D-Laws-12 (E5 R5 L5 Layer 1) | |
| 71 | F71 | 3D-Laws-13 (E5 R5 R5 Layer 1) | |
| 72 | F72 | 3D-Laws-14 (E5 R5 S5 Layer 1) | |
| 73 | F73 | 3D-Laws-15 (E5 R5 W5 Layer 1) | |
| 74 | F74 | 3D-Laws-16 (E5 S5 E5 Layer 1) | |
| 75 | F75 | 3D-Laws-17 (E5 S5 L5 Layer 1) | |
| 76 | F76 | 3D-Laws-18 (E5 S5 R5 Layer 1) | |
| 77 | F77 | 3D-Laws-19 (E5 S5 S5 Layer 1) | |
| 78 | F78 | 3D-Laws-20 (E5 S5 W5 Layer 1) | |
| 79 | F79 | 3D-Laws-21 (E5 W5 E5 Layer 1) | |
| 80 | F80 | 3D-Laws-22 (E5 W5 L5 Layer 1) | |
| 81 | F81 | 3D-Laws-23 (E5 W5 R5 Layer 1) | |
| 82 | F82 | 3D-Laws-24 (E5 W5 S5 Layer 1) | |
| 83 | F83 | 3D-Laws-25 (E5 W5 W5 Layer 1) | |
| 84 | F84 | 3D-Laws-26 (L5 E5 E5 Layer 1) | |
| 85 | F85 | 3D-Laws-27 (L5 E5 L5 Layer 1) | |
| 86 | F86 | 3D-Laws-28 (L5 E5 R5 Layer 1) | |
| 87 | F87 | 3D-Laws-29 (L5 E5 S5 Layer 1) | |
| 88 | F88 | 3D-Laws-30 (L5 E5 W5 Layer 1) | |
| 89 | F89 | 3D-Laws-31 (L5 L5 E5 Layer 1) | |
| 90 | F90 | 3D-Laws-32 (L5 L5 L5 Layer 1) | |
| 91 | F91 | 3D-Laws-33 (L5 L5 R5 Layer 1) | |
| 92 | F92 | 3D-Laws-34 (L5 L5 S5 Layer 1) | |
| 93 | F93 | 3D-Laws-35 (L5 L5 W5 Layer 1) | |
| 94 | F94 | 3D-Laws-36 (L5 R5 E5 Layer 1) | |
| 95 | F95 | 3D-Laws-37 (L5 R5 L5 Layer 1) | |
| 96 | F96 | 3D-Laws-38 (L5 R5 R5 Layer 1) | |
| 97 | F97 | 3D-Laws-39 (L5 R5 S5 Layer 1) | |
| 98 | F98 | 3D-Laws-40 (L5 R5 W5 Layer 1) | |
| 99 | F99 | 3D-Laws-41 (L5 S5 E5 Layer 1) | |
| 100 | F100 | 3D-Laws-42 (L5 S5 L5 Layer 1) | |
| 101 | F101 | 3D-Laws-43 (L5 S5 R5 Layer 1) | |
| 102 | F102 | 3D-Laws-44 (L5 S5 S5 Layer 1) | |
| 103 | F103 | 3D-Laws-45 (L5 S5 W5 Layer 1) | |
| 104 | F104 | 3D-Laws-46 (L5 W5 E5 Layer 1) | |
| 105 | F105 | 3D-Laws-47 (L5 W5 L5 Layer 1) | |
| 106 | F106 | 3D-Laws-48 (L5 W5 R5 Layer 1) | |
| 107 | F107 | 3D-Laws-49 (L5 W5 S5 Layer 1) | |
| 108 | F108 | 3D-Laws-50 (L5 W5 W5 Layer 1) | |
| 109 | F109 | 3D-Laws-51 (R5 E5 E5 Layer 1) | |
| 110 | F110 | 3D-Laws-52 (R5 E5 L5 Layer 1) | |
| 111 | F111 | 3D-Laws-53 (R5 E5 R5 Layer 1) | |
| 112 | F112 | 3D-Laws-54 (R5 E5 S5 Layer 1) | |
| 113 | F113 | 3D-Laws-55 (R5 E5 W5 Layer 1) | |
| 114 | F114 | 3D-Laws-56 (R5 L5 E5 Layer 1) | |
| 115 | F115 | 3D-Laws-57 (R5 L5 L5 Layer 1) | |
| 116 | F116 | 3D-Laws-58 (R5 L5 R5 Layer 1) | |
| 117 | F117 | 3D-Laws-59 (R5 L5 S5 Layer 1) | |

TABLE A2-continued

Description of Quantitative Feature Used to Describe Tumor Objects (e.g., a lung tumor)

| Sno | Feature Index | Description of the Features | Feature Category |
|---|---|---|---|
| 118 | F118 | 3D-Laws-60 (R5 L5 W5 Layer 1) | |
| 119 | F119 | 3D-Laws-70 (R5 R5 E5 Layer 1) | |
| 120 | F120 | 3D-Laws-71 (R5 R5 L5 Layer 1) | |
| 121 | F121 | 3D-Laws-72 (R5 R5 R5 Layer 1) | |
| 122 | F122 | 3D-Laws-73 (R5 R5 S5 Layer 1) | |
| 123 | F123 | 3D-Laws-74 (R5 R5 W5 Layer 1) | |
| 124 | F124 | 3D-Laws-75 (R5 S5 E5 Layer 1) | |
| 125 | F125 | 3D-Laws-76 (R5 S5 L5 Layer 1) | |
| 126 | F126 | 3D-Laws-77 (R5 S5 R5 Layer 1) | |
| 127 | F127 | 3D-Laws-78 (R5 S5 S5 Layer 1) | |
| 128 | F128 | 3D-Laws-79 (R5 S5 W5 Layer 1) | |
| 129 | F129 | 3D-Laws-80 (R5 W5 E5 Layer 1) | |
| 130 | F130 | 3D-Laws-81 (R5 W5 L5 Layer 1) | |
| 131 | F131 | 3D-Laws-82 (R5 W5 R5 Layer 1) | |
| 132 | F132 | 3D-Laws-83 (R5 W5 S5 Layer 1) | |
| 133 | F133 | 3D-Laws-84 (R5 W5 W5 Layer 1) | |
| 134 | F134 | 3D-Laws-85 (S5 E5 E5 Layer 1) | |
| 135 | F135 | 3D-Laws-86 (S5 E5 L5 Layer 1) | |
| 136 | F136 | 3D-Laws-87 (S5 E5 R5 Layer 1) | |
| 137 | F137 | 3D-Laws-88 (S5 E5 S5 Layer 1) | |
| 138 | F138 | 3D-Laws-89 (S5 E5 W5 Layer 1) | |
| 139 | F139 | 3D-Laws-90 (S5 L5 E5 Layer 1) | |
| 140 | F140 | 3D-Laws-91 (S5 L5 L5 Layer 1) | |
| 141 | F141 | 3D-Laws-92 (S5 L5 R5 Layer 1) | |
| 142 | F142 | 3D-Laws-93 (S5 L5 S5 Layer 1) | |
| 143 | F143 | 3D-Laws-94 (S5 L5 W5 Layer 1) | |
| 144 | F144 | 3D-Laws-95 (S5 R5 E5 Layer 1) | |
| 145 | F145 | 3D-Laws-96 (S5 R5 L5 Layer 1) | |
| 146 | F146 | 3D-Laws-97 (S5 R5 R5 Layer 1) | |
| 147 | F147 | 3D-Laws-98 (S5 R5 S5 Layer 1) | |
| 148 | F148 | 3D-Laws-99 (S5 R5 W5 Layer 1) | |
| 149 | F149 | 3D-Laws-100 (S5 S5 E5 Layer 1) | |
| 150 | F150 | 3D-Laws-101 (S5 S5 L5 Layer 1) | |
| 151 | F151 | 3D-Laws-102 (S5 S5 R5 Layer 1) | |
| 152 | F152 | 3D-Laws-103 (S5 S5 S5 Layer 1) | |
| 153 | F153 | 3D-Laws-104 (S5 S5 W5 Layer 1) | |
| 154 | F154 | 3D-Laws-105 (S5 W5 E5 Layer 1) | |
| 155 | F155 | 3D-Laws-106 (S5 W5 L5 Layer 1) | |
| 156 | F156 | 3D-Laws-107 (S5 W5 R5 Layer 1) | |
| 157 | F157 | 3D-Laws-108 (S5 W5 S5 Layer 1) | |
| 158 | F158 | 3D-Laws-109 (S5 W5 W5 Layer 1) | |
| 159 | F159 | 3D-Laws-110 (W5 E5 E5 Layer 1) | |
| 160 | F160 | 3D-Laws-111 (W5 E5 L5 Layer 1) | |
| 161 | F161 | 3D-Laws-112 (W5 E5 R5 Layer 1) | |
| 162 | F162 | 3D-Laws-113 (W5 E5 S5 Layer 1) | |
| 163 | F163 | 3D-Laws-114 (W5 E5 W5 Layer 1) | |
| 164 | F164 | 3D-Laws-115 (W5 L5 E5 Layer 1) | |
| 165 | F165 | 3D-Laws-116 (W5 L5 L5 Layer 1) | |
| 166 | F166 | 3D-Laws-117 (W5 L5 R5 Layer 1) | |
| 167 | F167 | 3D-Laws-118 (W5 L5 S5 Layer 1) | |
| 168 | F168 | 3D-Laws-119 (W5 L5 W5 Layer 1) | |
| 169 | F169 | 3D-Laws-120 (W5 R5 E5 Layer 1) | |
| 170 | F170 | 3D-Laws-121 (W5 R5 L5 Layer 1) | |
| 171 | F171 | 3D-Laws-122 (W5 R5 R5 Layer 1) | |
| 172 | F172 | 3D-Laws-123 (W5 R5 S5 Layer 1) | |
| 173 | F173 | 3D-Laws-124 (W5 S5 E5 Layer 1) | |
| 174 | F174 | 3D-Laws-125 (W5 S5 L5 Layer 1) | |
| 175 | F175 | 3D-Laws-126 (W5 R5 W5 Layer 1) | |
| 176 | F176 | 3D-Laws-127 (W5 S5 R5 Layer 1) | |
| 177 | F177 | 3D-Laws-128 (W5 S5 S5 Layer 1) | |
| 178 | F178 | 3D-Laws-129 (W5 S5 W5 Layer 1) | |
| 179 | F179 | 3D-Laws-130 (W5 W5 E5 Layer 1) | |
| 180 | F180 | 3D-Laws-131 (W5 W5 L5 Layer 1) | |
| 181 | F181 | 3D-Laws-132 (W5 W5 R5 Layer 1) | |
| 182 | F182 | 3D-Laws-133 (W5 W5 S5 Layer 1) | |
| 183 | F183 | 3D-Laws-134 (W5 W5 W5 Layer 1) | |
| 190 | F190 | 3D-Wave-1 (P2 L2 C9 Layer 1) | C7. Wavelets Texture (feature at different layers) |
| 191 | F191 | 3D-Wave-2 (P1 L2 C9 Layer 1) | |
| 192 | F192 | 3D-Wave-3 (P2 L2 C10 Layer 1) | |
| 193 | F193 | 3D-Wave-4 (P2 L2 C11 Layer 1) | |
| 194 | F194 | 3D-Wave-5 (P2 L2 C12 Layer 1) | |
| 195 | F195 | 3D-Wave-6 (P2 L2 C13 Layer 1) | |
| 196 | F196 | 3D-Wave-7 (P2 L2 C14 Layer 1) | |
| 197 | F197 | 3D-Wave-8 (P2 L2 C15 Layer 1) | |

TABLE A2-continued

Description of Quantitative Feature Used to Describe Tumor Objects (e.g., a lung tumor)

| Sno | Feature Index | Description of the Features | Feature Category |
|-----|---------------|------------------------------|------------------|
| 198 | F198 | 3D-Wave-9 (P2 L2 C1 Layer 1) | |
| 199 | F199 | 3D-Wave-10 (P2 L2 C2 Layer 1) | |
| 200 | F200 | 3D-Wave-11 (P2 L2 C3 Layer 1) | |
| 201 | F201 | 3D-Wave-12 (P2 L2 C4 Layer 1) | |
| 202 | F202 | 3D-Wave-13 (P2 L2 C5 Layer 1) | |
| 203 | F203 | 3D-Wave-14 (P2 L2 C6 Layer 1) | |
| 204 | F204 | 3D-Wave-15 (P2 L2 C7 Layer 1) | |
| 205 | F205 | 3D-Wave-16 (P2 L2 C8 Layer 1) | |
| 206 | F206 | 3D-Wave-17 (P1 L2 C11 Layer 1) | |
| 207 | F207 | 3D-Wave-18 (P1 L2 C10 Layer 1) | |
| 208 | F208 | 3D-Wave-19 (P1 L2 C12 Layer 1) | |
| 209 | F209 | 3D-Wave-20 (P1 L2 C13 Layer 1) | |
| 210 | F210 | 3D-Wave-21 (P1 L2 C14 Layer 1) | |
| 211 | F211 | 3D-Wave-22 (P1 L2 C15 Layer 1) | |
| 212 | F212 | 3D-Wave-23 (P1 L2 C1 Layer 1) | |
| 213 | F213 | 3D-Wave-24 (P1 L2 C2 Layer 1) | |
| 214 | F214 | 3D-Wave-25 (P1 L2 C3 Layer 1) | |
| 215 | F215 | 3D-Wave-26 (P1 L2 C4 Layer 1) | |
| 216 | F216 | 3D-Wave-27 (P1 L2 C5 Layer 1) | |
| 217 | F217 | 3D-Wave-28 (P1 L2 C6 Layer 1) | |
| 218 | F218 | 3D-Wave-29 (P1 L2 C7 Layer 1) | |
| 219 | F219 | 3D-Wave-30 (P1 L2 C8 Layer 1) | |

*See description in (1)

At 108, the tumor object is classified based on the extracted quantitative features. Optionally, classifying the tumor object based on the extracted quantitative features is predicting whether the tumor object is a malignant or benign tumor. Alternatively or additionally, the tumor object can be classified using a decision tree algorithm, a nearest neighbor algorithm or a support vector machine. It should be understood that these classification algorithms are provided only as examples and that other known classification algorithms can be used.

Optionally, it is possible to reduce the extracted quantitative features to a subset of extracted quantitative features, and then classify the tumor object based on the subset of extracted quantitative features. For example, the subset of extracted quantitative features can optionally include one or more quantitative features that are predictive of the classification of the tumor object. In other words, instead of classifying the tumor object based on the full set of extracted quantitative features, it is possible to classify the tumor object on a subset of extracted quantitative features having predictive value. This reduction of extracted quantitative features is described in detail below. Alternatively or additionally, the subset of extracted quantitative features can optionally include one or more non-redundant quantitative features having adequate reproducibility and dynamic range. In other words, it is possible to reduce the extracted quantitative features by eliminating quantitative features having lower reproducibility metrics and/or lower dynamic range, as well as redundant quantitative features. This reduction of extracted quantitative features is also described in detail below.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 4:
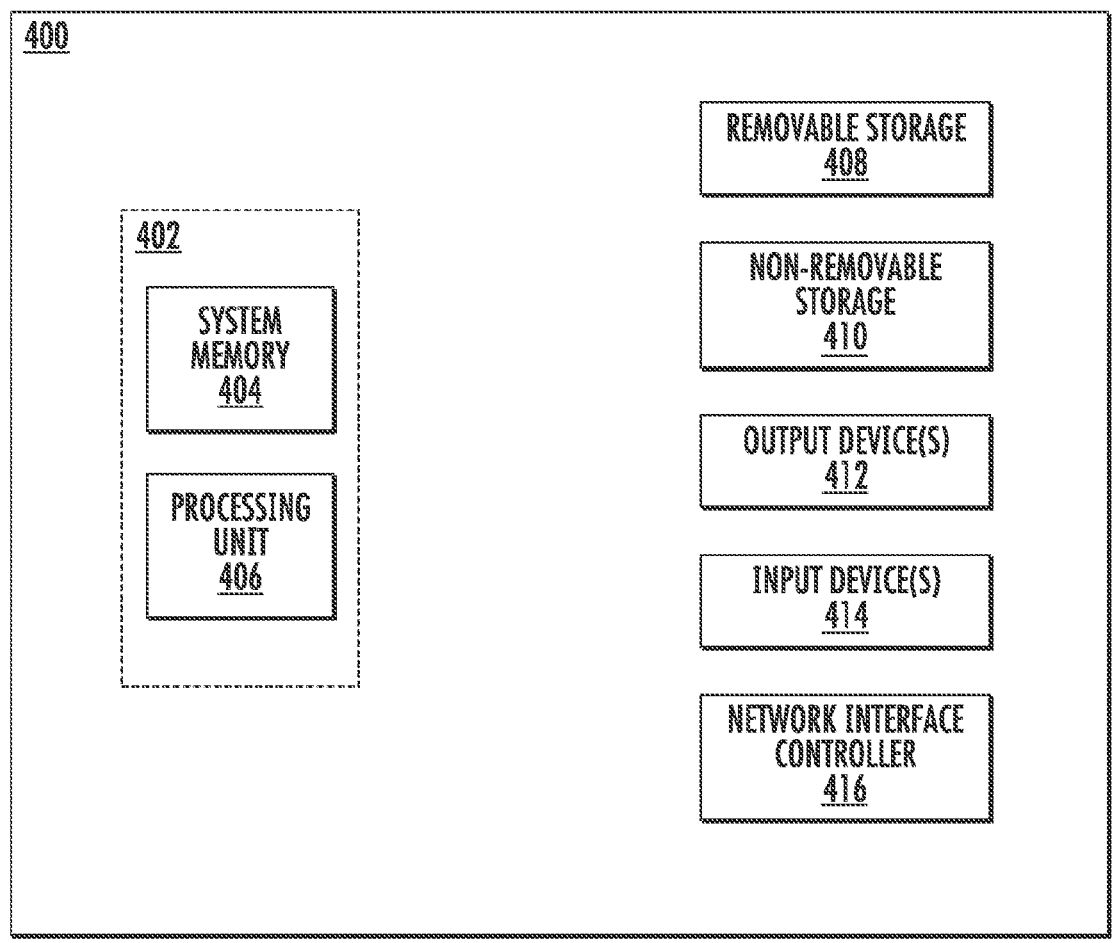
FIG. 4 is a block diagram of an example computing device.

When the logical operations described herein are implemented in software, the process may execute on any type of computing architecture or platform. For example, referring to FIG. 4, an example computing device upon which embodiments of the invention may be implemented is illustrated. The computing device 400 may include a bus or other communication mechanism for communicating information among various components of the computing device 400. In its most basic configuration, computing device 400 typically includes at least one processing unit 406 and system memory 404. Depending on the exact configuration and type of computing device, system memory 404 may be volatile (such as random access memory (RAM)), non-volatile (such as read-only memory (ROM), flash memory, etc.), or some combination of the two. This most basic configuration is illustrated in FIG. 4 by dashed line 402. The processing unit 406 may be a standard programmable processor that performs arithmetic and logic operations necessary for operation of the computing device 400.

Computing device 400 may have additional features/functionality. For example, computing device 400 may include additional storage such as removable storage 408 and non-removable storage 410 including, but not limited to, magnetic or optical disks or tapes. Computing device 400 may also contain network connection(s) 416 that allow the device to communicate with other devices. Computing device 400 may also have input device(s) 414 such as a keyboard, mouse, touch screen, etc. Output device(s) 412 such as a display, speakers, printer, etc. may also be included. The additional devices may be connected to the bus in order to facilitate communication of data among the components of the computing device 400. All these devices are all well known in the art and need not be discussed at length here.

The processing unit 406 may be configured to execute program code encoded in tangible, computer-readable media. Computer-readable media refers to any media that is capable of providing data that causes the computing device 400 (i.e., a machine) to operate in a particular fashion. Various computer-readable media may be utilized to provide instructions to the processing unit 406 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 406 may execute program code stored in the system memory 404. For example, the bus may carry data to the system memory 404, from which the processing unit 406 receives and executes instructions. The data received by the system memory 404 may optionally be stored on the removable storage 408 or the non-removable storage 410 before or after execution by the processing unit 406.

Computing device 400 typically includes a variety of computer-readable media. Computer-readable media can be any available media that can be accessed by device 400 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 404, removable storage 408, and non-removable storage 410 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 400. Any such computer storage media may be part of computing device 400.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

Methods

As described above, the process of diagnosis consists of lung field segmentation, pulmonary nodule segmentation, feature extraction, and classification is shown in FIG. 1. The CT images were acquired from the Lung Image Database Consortium (LIDC) in DICOM format. Lung Field Segmentation was accomplished by using the DEFINIENS LUNG TUMOR ANALYSIS software suite of DEFINIENS AG of MUNICH, GERMANY. Initial nodule segmentation was also accomplished by using the DEFINIENS LUNG TUMOR ANALYSIS software suite. Final segmentation and feature extraction was performed using the Single Click Ensemble Segmentation Algorithm, which is describe in Y. Gu et al., "Automated delineation of lung tumors from CT images using a single click ensemble segmentation approach," Pattern Recognition, vol. 46, no. 3, pp. 692-702 (2013), available at http://www.sciencedirect.com/science/article/pii/S0031320312004384. Feature selection was performed using the Weka toolkit, which is a suit of machine learning software developed at the University of Waikato, New Zealand and available at http://www.cs.waikato.ac.nz/ml/index.html, and a correlated feature selection algorithm. Predictive Models were constructed using 10-fold cross validation to create training and test data sets. Overall accuracy, sensitivity, and specificity were recorded along with Area under the curve (AUC). The following sections further describe the workflow process.

CT Image Data Set

The CT images were taken from the Lung Image Database Consortium and Image Database Resource Initiative (LIDC/IDRI) image collections; these collections are publicly available databases containing lung cancer diagnostic and screening images from thoracic CT.

As used herein, "low dose" is a threshold of 40 milliampere-seconds (mAs) for this study. Additionally, only cases with a known diagnosis were selected; cases where it is unclear which nodule is being diagnosed were eliminated.

This yields a total of 33 cases that meet the appropriate criteria. Of these cases, 14 were malignant and 19 were benign.

Segmentation and Feature Extraction

The lung field segmentation was performed by the automated organ segmentation procedure in the Lung Tumor Analysis (LuTA) software suite, which is a part of DEFINIENS LUNG TUMOR ANALYSIS software suite. Preliminary nodule segmentation was performed with the LuTA software using the published nodule location as the initial seed in a region growing algorithm. Final segmentation and 3D reconstruction was accomplished using a Single Click Ensemble Segmentation Algorithm as described above. From the segmented nodule regions, 219 2D and 3D image features were extracted which include texture features, intensity-based features, morphological features, and geometric features. An example segmented ROI 202 in a radiological image is shown in FIG. 2. In particular, the segmented ROI 202 is a segmented lung field in FIG. 2. The lung field has been demarcated by white boundary lines for visualization. An example segmented tumor object 302 in a radiological image is shown in FIG. 3. In particular, the segmented tumor object 302 is a segmented pulmonary nodule in FIG. 3. The pulmonary nodule has been bounded by white lines for visualization.

Classifiers and Feature Selection

Several commonly used classifiers were tested with texture features, shape features and with a combination of texture and shape features. The classifiers were evaluated through 10-fold (10-fold CV) cross-validation. The classification accuracy, sensitivity, and specificity were recorded for analysis.

1) Decision Tree: A decision tree is a predictive model where nodes are tests conducted on a single data element and leaves are class indicators. The decision tree classifiers used were J48 (Weka implementation of C4.5 Decision Tree) and the Weka implementation of Random Forests.

2) Nearest Neighbor: A nearest neighbor algorithm is an example of instance based learning where classification is determined by the most common class among the nearest neighbors. The Weka implementation of the k-Nearest-Neighbor algorithm (IBk) was used, with k=5.

3) Support Vector Machine: A support vector machine is a supervised learning model that non-linearly maps input data to a higher dimension feature space. An example SVM implementation is described in C.-C. Chang and C.-J. Lin, "Libsvm: A library for support vector machines," ACM Trans. Intell. Syst. Technol., vol. 2, no. 3, pp. 27:1-27:27, May 2011, available at http://doi.acm.org/10.1145/1961189.1961199. Tuning of the Radial Basis Function kernel used in the SVM was accomplished by using a grid search to provide optimized gamma and cost parameters.

4) Rule Based Classification: The rule based classifier used was Weka's JRIP, an implementation of the RIPPER algorithm by Cohen. This algorithm consists of two stages. In the grow phase, a rule is extended greedily by adding antecedents until the rule has perfect accuracy. Then in the prune phase the rule is pruned by removing antecedent conditions based on a metric and a pruning data set. Growing and pruning are repeated while there are positive examples or until the error rate exceeds 50%. Finally, rules that would add to the description length are deleted.

5) Naive Bayes: The Naive Bayes classifier, is designed to be used when features are independent of one another within each class. However, it has been shown that it often works well even when the features are not independent. The Naive Bayes classifier estimates the parameters of a probability distribution given the class, assuming features are conditionally independent. It then computes the posterior probability of a sample belonging to each class and puts the test sample into the class with the largest posterior probability. The assumption of class-conditional independence greatly simplifies the training step. Even though the class-conditional independence between features does not hold for most data sets, this optimistic assumption works well in practice. The implementation for Naive Bayes used for this work was from Weka.

6) Support Vector Machines: Support vector machines are based on statistical learning theory developed by Cortes and Vapnik and have been shown by Kramer et al., among others, to obtain high accuracy on a diverse range of application domains such as the letter, page, pendigit, satimage, and waveform data sets. SVMs map the input data to a higher dimensional feature space and construct a hyperplane to maximize the margin between classes. A linear decision surface is constructed in this feature space. The hyperplane construction can be reduced to a quadratic optimization problem; subsets of training patterns that lie on the margin were termed support vectors by Cortes and Vapnik. The formulation used herein allows for "errors" to be on the wrong side of the decision border during training. A cost parameter C is multiplied by the distance the errant example is from the decision boundary. The larger the value of C the larger the penalty applied in the learning process. Different kernels, such as a linear kernel, radial basis function kernel, and sigmoid kernel, can be chosen for SVMs. The linear kernel is used herein. Dehmeshki et al. used support vector machines effectively on CT-scan image data of the lungs in a Computer-Assisted Detection (CAD) system for automated pulmonary nodule detection in thoracic CT-scan images. The support vector machine libSVM by Chang and Lin was used. Parameter tuning of the cost parameter was conducted on training data using a grid search after feature selection.

7) Feature Selection: To avoid over-fitting of the data, primary feature set reduction was performed using the Weka implementation of Recursive Elimination of Features (Relief-F). Relief-F uses a nearest-neighbor approach to find features that distinguish between similar examples of differing classes.

Computed image features can have a high correlation with each other. This property combined with the fact that the number of features available to us was much greater than the number of examples required the investigation of feature selection techniques to improve classification accuracy. Feature selection was done per fold. Leave-one-out cross validation (LOO) was conducted on the data. In addition to feature selection, some of the classifiers' models do implicit feature selection. For instance, the decision tree and rule based classifiers subselect features. Also, support vector machines weight features. However, Naive Bayes uses all provided features for classification of the test set. All of classifiers explore all of the features to build models on the training set.

1) All Features: This group includes all 219-image features. No feature selection was performed, thus providing a baseline for the effectiveness of the feature selection techniques.

2) Relief-F: The Relief-F algorithm is a feature evaluator that compares an instance's feature value to the nearest neighbor of both the same and opposite classes. In this work, Relief-F was used to assign ranks to each individual feature. The top five and ten features found by the algorithm as shown in Table A. The top ranked features measure tumor attachment to the wall of the lung.

3) Correlation based Feature Selection (CFS): Correlation based Feature Selection (CFS) searches for features that correlate to a class but do not correlate with each other. The implementation used was found in WEKA. CFS discretizes attributes for nominal classes. The features chosen are shown in Table B. It can be seen that CFS prefers texture features with a few shape features when compared to the choices of Relief-F. Relief-F focuses on pleural wall attachment type features.

4) Test-retest: Test-retest features were determined by comparing the stability of features generated after two different scans of the same patient fifteen minutes apart [13]. If a feature is repeatable then the two subsequent scans should yield a similar value. The tumor was segmented both manually by a radiologist and with a single click ensemble approach. Different thresholds of correlation were used. Attributes were kept that had a test-retest concordance measured by a concordance correlation coefficient (CCC) of above 0.85, 0.90, and 0.95. At each correlation threshold different attributes were found using the manual and ensemble segmentation methods as well as the intersection of both.

TABLE B1

| Feature Selection | Count | Feature Name |
|---|---|---|
| Top 5 Relief-f | 40 | X8d_3D_Ratio_Free_To_Attached |
| Top 5 Relief-f | 40 | X8a_3D_Is_Attached_To_Pleural_Wall |
| Top 5 Relief-f | 40 | X8c_3D_Relative_Border_To_PleuralWall |
| Top 5 Relief-f | 40 | X8b_3D_Relative_Border_To_Lung |
| Top 5 Relief-f | 40 | X3D.Wavelet.decomposition...P1.L2.C14.Layer.1 |
| Top 10 Relief-f | 40 | X8d_3D_Ratio_Free_To_Attached |
| Top 10 Relief-f | 40 | X8a_3D_Is_Attached_To_Pleural_Wall |
| Top 10 Relief-f | 40 | X8c_3D_Relative_Border_To_PleuralWall |
| Top 10 Relief-f | 40 | X8b_3D_Relative_Border_To_Lung |
| Top 10 Relief-f | 40 | X3D.Wavelet.decomposition...P1.L2.C14.Layer.1 |
| Top 10 Relief-f | 40 | X3D.Wavelet.decomposition...P1.L2.C10.Layer.1 |
| Top 10 Relief-f | 39 | X3D.Laws.features...E5.S5.R5.Layer.1 |
| Top 10 Relief-f | 31 | X3D.Laws.features...W5.W5.L5.Layer.1 |
| Top 10 Relief-f | 21 | X3D.Laws.features...L5.S5.W5.Layer.1 |
| Top 10 Relief-f | 5 | X3D.Wavelet.decomposition...P1.L2.C9.Layer.1 |
| Top 10 Relief-f | 13 | avgLRE |
| Top 10 Relief-f | 11 | avgSRE |
| Top 10 Relief-f | 7 | X3D.Laws.features...L5.L5.S5.Layer.1 |
| Top 10 Relief-f | 8 | X3D.Laws.features...W5.E5.L5.Layer.1 |
| Top 10 Relief-f | 2 | X3D.Laws.features...S5.S5.E5.Layer.1 |
| Top 10 Relief-f | 2 | X3D.Laws.features...W5.S5.L5.Layer.1 |
| Top 10 Relief-f | 2 | X3D.Wavelet.decomposition...P1.L2.C11.Layer.1 |
| Top 10 Relief-f | 4 | X3D.Laws.features...S5.S5.W5.Layer.1 |
| Top 10 Relief-f | 8 | X3D.Laws.features...S5.L5.E5.Layer.1 |
| Top 10 Relief-f | 3 | X5a_3D_MacSPic_NumberOf |
| Top 10 Relief-f | 2 | Histogram.ENERGY.Layer.1 |
| Top 10 Relief-f | 1 | X3D.Laws.features...R5.E5.L5.Layer.1 |
| Top 10 Relief-f | 1 | X3D.Laws.features...E5.S5.W5.Layer.1 |

TABLE B2

| Feature Selection | Count | Feature Name |
|---|---|---|
| Top 5 CFS | 40 | X3D.Laws.features...W5.S5.R5.Layer.1 |
| Top 5 CFS | 40 | X3D.Laws.features...W5.S5.W5.Layer.1 |
| Top 5 CFS | 13 | X3D.Laws.features...R5.S5.S5.Layer.1 |
| Top 5 CFS | 13 | X3D.Laws.features...S5.S5.W5.Layer.1 |
| Top 5 CFS | 14 | X3D.Laws.features...W5.S5.S5.Layer.1 |
| Top 5 CFS | 28 | Longest.Diameter...mm. |
| Top 5 CFS | 26 | Short.Axis...Longest.Diameter...mm... |
| Top 5 CFS | 24 | Short.Axis...mm. |
| Top 5 CFS | 1 | X3D.Laws.features...S5.S5.R5.Layer.1 |
| Top 10 CFS | 1 | X3D.Wavelet.decomposition...P1.L2.C4.Layer.1 |
| Top 10 CFS | 40 | X3D.Laws.features...W5.S5.R5.Layer.1 |

TABLE B2-continued

| Feature Selection | Count | Feature Name |
|---|---|---|
| Top 10 CFS | 40 | X3D.Laws.features...W5.S5.W5.Layer.1 |
| Top 10 CFS | 13 | X3D.Laws.features...R5.S5.S5.Layer.1 |
| Top 10 CFS | 13 | X3D.Laws.features...S5.S5.W5.Layer.1 |
| Top 10 CFS | 14 | X3D.Laws.features...W5.S5.S5.Layer.1 |
| Top 10 CFS | 40 | Longest.Diameter...mm. |
| Top 10 CFS | 40 | Short.Axis...Longest.Diameter...mm... |
| Top 10 CFS | 40 | Short.Axis...mm. |
| Top 10 CFS | 40 | Mean...HU. |
| Top 10 CFS | 40 | StdDev...HU. |
| Top 10 CFS | 28 | Volume...cm... |
| Top 10 CFS | 26 | X5a_3D_MacSpic_NumberOf |
| Top 10 CFS | 24 | X8a_3D_Is_Attached_To_Pleural_Wall |
| Top 10 CFS | 1 | X3D.Laws.features...S5.S5.R5.Layer.1 |
| Top 10 CFS | 1 | X3D.Wavelet.decomposition...P1.L2.C4.Layer.1 |

The results of running Pearson Product-Moment Correlation Coefficient on the data set indicated that a large number of features had a high degree of correlation/anti-correlation. Since Relief-F does not calculate the correlation between features, the Weka implementation of Correlation-based Feature Subset Selection for Machine Learning (CFS) was explored. This algorithm selects features that are predictive of the class using Pearson's Coefficient while eliminating those that have a high degree of correlation with each other (also based on Pearson's Coefficient). Additionally, an algorithm referred to herein as "Relief-F Non-Correlated" ("RFNC") (also referred to herein as Relief-F with Correlation Detection algorithm) that used the Relief-F rankings to determine class predictability while eliminating correlated features where the Pearson's Coefficient exceeded a specified threshold was developed.

Feature selection for all experiments was performed on the entire data set using Leave-One-Volume-Out cross validation resulting in an optimistic feature set. For Relief-F, the features with the highest average merit were selected. For CFS, all features were selected that appeared in more than 50% of the folds.

Experiments

Segmentation and feature extraction were performed on 33 cases from the LIDC data set, consisting of 14 malignant and 19 benign nodules. Attribute values were normalized −1 to 1. Experiments were conducted using three separate sets of features. The first set consisted of 47 shape features, the second of 172 texture features, and the third is a combined set of 219 features. Training and testing data sets were generated using 10-fold cross validation.

For each classifier and data set, experiments were performed using a data set that consisted of all features (no feature selection), feature sets consisting of the top 10 and top 5 Relief-F features, a set of 5 features based on CFS (4 features in the case for the shape-feature data set), and sets of features consisting of the top five non-correlated Relief-F features with Pearson's Coefficient thresholds of 0.8 and 0.5.

Results

All experiments resulted in accuracies that exceeded guessing the majority class (57.57%). Table I shows the classification accuracy achieved by different classifiers using 47 shape features. The highest accuracy of 81.82% was achieved using J48 with CFS feature selection (4 features).

TABLE I

PERFORMANCE OF CLASSIFIERS WITH 47 SHAPE FEATURES

| Classifier | Feat. Sel. | Accuracy | Sensitivity | Specificity |
|---|---|---|---|---|
| J48 | All Features | 75.76% | 71.43% | 78.95% |
|  | Relief-F | 78.79% | 71.43% | 84.21% |
|  | CFS | 81.32% | 71.43% | 89.47% |
|  | RFNC .80 | 72.73% | 57.14% | 82.21% |
|  | RFNC .50 | 75.76% | 57.14% | 89.47% |
| Random Forest | All Features | 75.76% | 71.43% | 78.95% |
|  | Relief-F | 69.7% | 64.29% | 72.63% |
|  | CFS | 60.61% | 42.86% | 73.63% |
|  | RFNC .80 | 69.70% | 71.43% | 68.42% |
|  | RFNC .50 | 72.73% | 71.43% | 73.68% |
| IBk (5 NN) | All Features | 78.79% | 64.29% | 89.47% |
|  | Relief-F | 63.64% | 42.86% | 78.95% |
|  | CFS | 72.73% | 50.00% | 89.47% |
|  | RFNC .80 | 78.79% | 64.29% | 89.47% |
|  | RFNC .50 | 75.76% | 57.14% | 89.47% |
| SVM | All Features | 63.64% | 42.86% | 78.95% |
|  | Relief-F | 72.73% | 50.00% | 89.47% |
|  | CFS | 72.73% | 57.14% | 84.21% |
|  | RFNC .80 | 69.70% | 57.14% | 78.95% |
|  | RFNC .50 | 73.79% | 64.29% | 89.47% |

Table II shows the results of the same classifiers using only texture features. Accuracy generally increased with a few exceptions. Moreover, the best accuracy of 90.91% was achieved using IBk (5 NN) with CFS feature selection.

TABLE II

PERFORMANCE OF CLASSIFIERS WITH 172 TEXTURE FEATURES

| Classifier | Feat. Sel. | Accuracy | Sensitivity | Specificity |
|---|---|---|---|---|
| J48 | All Features | 78.79% | 71.43% | 84.21% |
|  | Relief-F | 81.82% | 92.86% | 73.68% |
|  | CFS | 66.67% | 50.00% | 78.95% |
|  | RFNC .80 | 60.61% | 50.00% | 68.42% |
|  | RFNC .50 | 60.61% | 50.00% | 68.42% |
| Random Forest | All Features | 72.73% | 64.29% | 78.95% |
|  | Relief-F | 66.67% | 57.14% | 73.68% |
|  | CFS | 72.73% | 57.14% | 82.21% |
|  | RFNC .80 | 72.73% | 64.29% | 78.95% |
|  | RFNC .50 | 75.76% | 64.29% | 84.21% |
| IBk (5 NN) | All Features | 78.79% | 78.57% | 78.95% |
|  | Relief-F | 81.82% | 78.57% | 84.21% |
|  | CFS | 90.91% | 85.71% | 94.74% |
|  | RFNC .80 | 84.85% | 78.57% | 89.47% |
|  | RFNC .50 | 81.82% | 78.57% | 84.21% |
| SVM | All Features | 84.85% | 78.57% | 89.47% |
|  | Relief-F | 75.76% | 78.57% | 73.68% |
|  | CFS | 78.79% | 71.43% | 84.21% |
|  | RFNC .80 | 81.82% | 71.43% | 89.47% |
|  | RFNC .50 | 78.79% | 78.57% | 78.95% |

Table III shows the results using both texture and shape features. Accuracies generally improved over experiments using only shape or texture features. The highest accuracy was 87.88% using J48 with no feature selection and SVM using CFS.

TABLE III

PERFORMANCE OF CLASSIFIERS WITH 219 TEXTURE AND SHAPE FEATURES

| Classifier | Feat. Sel. | Accuracy | Sensitivity | Specificity |
|---|---|---|---|---|
| J48 | All Features | 87.88% | 85.71% | 89.47% |
|  | Relief-F | 81.82% | 92.86% | 73.68% |
|  | CFS | 69.70% | 57.14% | 78.95% |
|  | RFNC .80 | 69.70% | 57.14% | 78.95% |
|  | RFNC .50 | 66.67% | 50.00% | 78.95% |
| Random Forest | All Features | 72.73% | 57.14% | 84.21% |
|  | Relief-F | 66.67% | 57.14% | 73.68% |
|  | CFS | 75.76% | 57.14% | 89.47% |
|  | RFNC .80 | 72.73% | 71.43% | 73.68% |
|  | RFNC .50 | 66.67% | 57.14% | 73.68% |
| IBk (5 NN) | All Features | 84.85% | 78.57% | 89.47% |
|  | Relief-F | 81.82% | 78.57% | 84.21% |
|  | CFS | 81.82% | 71.43% | 89.47% |
|  | RFNC .80 | 87.88% | 78.57% | 94.74% |
|  | RFNC .50 | 75.76% | 57.14% | 89.47% |
| SVM | All Features | 84.85% | 78.57% | 89.47% |
|  | Relief-F | 75.76% | 78.57% | 73.68% |
|  | CFS | 87.88% | 85.71% | 89.47% |
|  | RFNC .80 | 87.88% | 78.57% | 94.74% |
|  | RFNC .50 | 78.79% | 64.29% | 89.47% |

Table IV shows the top shape features selected by Relief-F, Table V, the top texture features, and Table VI, the top features from the combined feature set.

TABLE IV

TOP RELIEF-F 47 SHAPE FEATURES
Feature Name

3D_SD_Dist_COG_To_Border
3D_Is_Attached_To_Pleural_Wall
3D_MAX_Dist_COG_To_Border
Longest Diameter
Length

TABLE V

TOP RELIEF-F 172 TEXTURE FEATURES
Feature Name

3D Wavelet decomposition. P2 L2 C8 Layer 1
3D Wavelet decomposition. P2 L2 C15 Layer 1
3D Wavelet decomposition. P2 L2 C1 Layer 1
3D Wavelet decomposition. P2 L2 C7 Layer 1
3D Wavelet decomposition. P2 L2 C4 Layer 1

TABLE VI

TOP RELIEF-F 219 TEXTURE AND SHAPE FEATURES
Feature Name

3D Wavelet decomposition P2 L2 C8 Layer 1
3D Wavelet decomposition P2 L2 C15 Layer 1
3D Wavelet decomposition P2 L2 C1 Layer 1
3D Wavelet decomposition P2 L2 C7 Layer 1
3D Wavelet decomposition P2 L2 C4 Layer 1

Tables VII, VIII and IX enumerate the features selected by the CFS algorithm from the shape-feature data set, the texture feature-only data set, and the combined data set respectively.

TABLE VII

CFS SELECTION FROM 47 SHAPE FEATURES
Feature Name

Longest Diameter
3D_Relative_Border_To_Lung
3D_MIN_Dist_COG_To_Border
Elliptic Fit

TABLE VIII

CFS SELECTION FROM 172 TEXTURE FEATURES
Feature Name avgCoocurrence-MP
3D Laws features L5 E5 R5 Layer 1
3D Wavelet decomposition. P2 L2 C1 Layer 1
3D Wavelet decomposition. P1 L2 C1 Layer 1
3D Wavelet decomposition. P1 L2 C2 Layer 1

TABLE IX

CFS SELECTION FROM 219 TEXTURE AND SHADE FEATURES
Feature Name

3D Laws features L5 E5 R5 Layer 1
3D Wavelet decomposition. P2 L2 C1 Layer 1
3D Wavelet decomposition. P1 L2 C1 Layer 1
3D Wavelet decomposition. P1 L2 C2 Layer 1
Elliptic Fit Tables X, XII, and XIV list the features selected by the RFNC algorithm with threshold 0.8 from the shape-feature data set, the texture-feature-only data set, and the combined data set; tables XI, XIII, and XV list the features selected for a threshold of 0.5.

TABLE X

RELIEF-F NON-CORRELATED SELECTION FROM 47 SHAPE FEATURES, THRESHOLD = 0.8
Feature Name 9e_3D_SD_Dist_COG_To_Border_[mm]
8d_3D_Ratio_Free_To_Attached
Rectangular Fit
Shape index
Histogram ENTROPY Layer 1

TABLE XI

RELIEF-F NON-CORRELATED SELECTION FROM 47 SHAPE FEATURES, THRESHOLD = 0.5
Feature Name 9e_3D_SD_Dist_COG_To_Border_[mm]
8d_3D_Ratio_Free_To_Attached
Histogram ENTROPY Layer 1
Histogram SKEW Layer 1
Asymmetry

TABLE XII

RELIEF-F NON-CORRELATED SELECTION FROM 172 TEXTURE FEATURES, THRESHOLD = 0.8
Feature Name 3D Wavelet decomposition. P2 L2 C8 Layer 1
avgRP
3D Laws features L5 E5 R5 Layer 1
3D Wavelet decomposition. P1 L2 C3 Layer 1
3D Laws features R5 E5 R5 Layer 1

TABLE XIII

RELIEF-F NON-CORRELATED SELECTION FROM 172 TEXTURE FEATURES, THRESHOLD = 0.5
Feature Name 3D Wavelet decomposition. P2 L2 C8 Layer 1
3D Laws features L5 E5 R5 Layer 1
3D Laws features R5 L5 R5 Layer 1
3D Laws features W5 E5 E5 Layer 1
avgCoocurrence-entropy

TABLE XIV

RELIEF-F NON-CORRELATED SELECTION FROM 219 TEXTURE AND SHAPE FEATURES, THRESHOLD = 0.8
Feature Name 3D Wavelet decomposition. P2 L2 C8 Layer 1
9e_3D_SD_Dist_COG_To_Border_[mm]
Rectangular Fit
3D Laws features L5 E5 R5 Layer 1
3D Wavelet decomposition. P1 L2 C3 Layer 1

TABLE XV

RELIEF-F NON-CORRELATED SELECTION FROM 219 TEXTURE AND SHAPE FEATURES, THRESHOLD = 0.5
Feature Name 3D Wavelet decomposition. P2 L2 C8 Layer 1
3D Laws features L5 E5 R5 Layer 1
8a_3D_Is_Attached_To_Pleural_Wall
Histogram ENTROPY Layer 1
Histogram SKEW Layer 1

For the shape-feature data set, feature selection yielded the same or better accuracies for the J48 and SVM classifiers as compared to no feature selection. Only IBk (5 NN) showed consistent improvement with feature selection on the texture-feature-only data set; the most notable improvement being the 90.91% accuracy reported earlier. Feature reduction on the combined data set produced mixed results.

The Correlation-based Feature Subset Selection (CFS) algorithm was most effective in conjunction with the J48 and SVM classifiers on the shape-feature data set and resulted in less effective feature sets in conjunction with the other classifiers. On both the texture and combined data sets, CFS resulted in effective reduced feature sets when using IBk (5 NN) and SVM.

CONCLUSION

The positive effect of texture features in the classification of pulmonary nodules in low-dose CT have been shown.

There were 219 image features extracted which included texture and shape features. The features were used for the classification of pulmonary nodules into malignant and benign using several classifiers like Decision Trees, Random Forests, Nearest Neighbors, and Support Vector Machines. While the best overall results were achieved using CFS feature selection and the IBk classifier with the texture-feature-only data set, more consistent results were obtained with the combined data set.

With a combination of texture and shape features, the highest accuracy achieved was 87.88%—an improvement over the 81.82% achieved when only the shape features were used. When using the SVM classifier and CFS feature selection, the sensitivity improved from 71.43% to 85.71% while the specificity remained the same at 89.47%. Similarly, the IBk (5 NN) classifier with a non-correlated Relief-F feature set, showed the same accuracy improvement with a sensitivity of 78.57% and a specificity of 94.74%.

Tables XVI-XXI show additional accuracy results based on feature selection method.

TABLE XVI

| Classifier | Features | # | Avg Accy | LQ Accy | UQ Accy | AUC |
|---|---|---|---|---|---|---|
| Decision Tree | Top 5 Relief-f | 5 | 77.5% | 65% | 90% | 0.712 |
| Decision Tree | Top 10 Relief-f | 10 | 70% | 65% | 75% | 0.732 |
| Rules | All | 219 | 62.5% | 65% | 60% | 0.729 |
| Rules | All Top 5 Relief-f | 5 | 75% | 65% | 85% | 0.661 |
| Naive Bayes | All Top 10 Relief-f | 10 | 65% | 55% | 75% | 0.52 |
| Naive Bayes | Manual & Ensemble test-retest (.85) Top 5 RF | 5 | 60% | 45% | 75% | 0.64 |
| SVM | Manual test-retest (.90) Top 10 Relief-f | 10 | 65% | 70% | 60% | 0.65 |

SUMMARY OF THE HIGHEST SURVIVAL LEAVE-ONE-OUT ACCURACY AND AUC RESULTS CONTAINING THE FEATURE SELECTION METHOD, NUMBER OF FEATURES, AVERAGE ACCURACY, LOWER QUARTILE ACCURACY, UPPER QUARTILE ACCURACY, AND THE AREA UNDER THE RECEIVER OPERATING CURVE. LQ IS LOWER QUARTILE AND UQ IS UPPER QUARTILE.

TABLE XVII

| Classifier | Features | # | Avg Accy | LQ Accy | UQ Accy | AUC |
|---|---|---|---|---|---|---|
| Decision Tree | Top 5 Relief-f | 5 | 77.5% | 65% | 90% | 0.712 |
| | Top 10 Relief-f | 10 | 70% | 65% | 75% | 0.732 |
| | All Top 5 CFS | 5 | 62.5% | 95% | 30% | 0.292 |
| | All Top 10 CFS | 10 | 65% | 75% | 55% | 0.552 |
| | Manual test-retest (.95) | 45 | 60% | 95% | 25% | 0.271 |
| | Manual test-retest (.90) Top 10 Relief-f | 10 | 67.5% | 70% | 65% | 0.562 |
| | Manual test-retest (.90) Top 10 CFS | 10 | 60% | 70% | 50% | 0.435 |
| | Manual test-retest (.85) Top 5 Relief-f | 5 | 62.5% | 85% | 40% | 0.455 |
| | Manual test-retest (.85) Top 5 CFS | 5 | 72.5% | 95% | 50% | 0.488 |
| | Manual test-retest (.85) Top 10 CFS | 10 | 62.5% | 70% | 55% | 0.51 |
| | Ensemble test-retest (.95) Top 5 CFS | 5 | 65% | 100% | 30% | 0.3 |
| | Ensemble test-retest (.95) Top 10 CFS | 10 | 65% | 100% | 30% | 0.3 |
| | Ensemble test-retest (.90) Top 5 CFS | 5 | 62.5% | 95% | 30% | 0.292 |
| | Ensemble test-retest (.90) Top 10 CFS | 10 | 65% | 75% | 55% | 0.524 |
| | Ensemble test-retest (.85) Top 5 CFS | 5 | 62.5% | 95% | 30% | 0.292 |
| | Ensemble test-retest (.85) Top 10 CFS | 10 | 65% | 75% | 55% | 0.524 |
| | Manual & Ensemble test-retest (.90) Top 10 Relief-f | 10 | 65% | 70% | 60% | 0.691 |
| | Manual & Ensemble test-retest (.85) Top 10 Relief-f | 10 | 62.5% | 65% | 60% | 0.68 |

SURVIVAL LEAVE-ONE-OUT ACCURACY RESULTS DOING FURTHER FEATURE SELECTION ON TEST-RETEST FEATURES FOR DECISION TREES CONTAINING THE FEATURE SELECTION METHOD, NUMBER OF FEATURES, AVERAGE ACCURACY, LOWER QUARTILE ACCURACY, UPPER QUARTILE ACCURACY, AND THE AREA UNDER THE RECEIVER OPERATING CURVE. THE TOP ACCURACY AND AUC ARE IN BOLD.

TABLE XVIII

| Classifier | Features | # | Avg Accy | LQ Accy | UQ Accy | AUC |
|---|---|---|---|---|---|---|
| Rules | All | 219 | 62.5% | 65% | 60% | 0.729 |
| | All Top 5 Relief-f | 5 | 75% | 65% | 85% | 0.661 |
| | All Top 10 Relief-f | 10 | 65% | 60% | 70% | 0.598 |
| | Manual test-retest (.90) Top 10 Relief-f | 10 | 62.5% | 75% | 50% | 0.568 |
| | Manual test-retest (.85) | 95 | 62.5% | 75% | 50% | 0.688 |

SURVIVAL LEAVE-ONE-OUT ACCURACY RESULTS DOING FURTHER FEATURE SELECTION ON TEST-RETEST FEATURES FOR JRIP CONTAINING THE FEATURE SELECTION METHOD, NUMBER OF FEATURES, AVERAGE ACCURACY, LOWER QUARTILE ACCURACY, UPPER QUARTILE ACCURACY, AND THE AREA UNDER THE RECEIVER OPERATING CURVE. THE TOP ACCURACY AND AUC ARE IN BOLD.

TABLE XIX

| Classifier | Features | # | Avg Accy | LQ Accy | UQ Accy | AUC |
|---|---|---|---|---|---|---|
| Naive Bayes | All Top 5 Relief-f | 5 | 62.5% | 45% | 80% | 0.605 |
| | All Top 10 Relief-f | 10 | 65% | 55% | 75% | 0.52 |
| | Manual test-retest (.95) Top 5 Relief-f | 5 | 60% | 40% | 80% | 0.458 |
| | Manual test-retest (.90) Top 5 Relief-f | 5 | 60% | 45% | 75% | 0.54 |
| | Manual & Ensemble test-retest (.95) Top 5 Relief-f | 5 | 60% | 40% | 80% | 0.552 |
| | Manual & Ensemble test-retest (.85) Top 5 RF | 5 | 60% | 45% | 75% | 0.64 |

SURVIVAL LEAVE-ONE-OUT ACCURACY RESULTS DOING FURTHER FEATURE SELECTION ON TEST-RETEST FEATURES FOR NAIVE BAYES CONTAINING THE FEATURE SELECTION METHOD, NUMBER OF FEATURES, AVERAGE ACCURACY, LOWER QUARTILE ACCURACY, UPPER QUARTILE ACCURACY, AND THE AREA UNDER THE RECEIVER OPERATING CURVE. THE TOP ACCURACY AND AUC ARE IN BOLD.

TABLE XX

| Classifier | Features | # | Avg Accy | LQ Accy | UQ Accy | AUC |
|---|---|---|---|---|---|---|
| SVM | Manual test-retest (.90) Top 10 Relief-f | 10 | 65% | 70% | 60% | 0.65 |
| | Manual & Ensemble test-retest (.90) Top 5 Relief-f | 5 | 62.5% | 65% | 60% | 0.625 |
| | Manual & Ensemble test-retest (.90) Top 10 Relief-f | 10 | 60% | 65% | 55% | 0.6 |
| | Manual & Ensemble test-retest (.85) Top 5 Relief-f | 5 | 62.5% | 65% | 60% | 0.625 |
| | Manual & Ensemble test-retest (.85) Top 10 Relief-f | 10 | 60% | 65% | 55% | 0.6 |

SURVIVAL LEAVE-ONE-OUT ACCURACY RESULTS DOING FURTHER FEATURE SELECTION ON TEST-RETEST FEATURES FOR SVM CONTAINING THE FEATURE SELECTION METHOD, NUMBER OF FEATURES, AVERAGE ACCURACY, LOWER QUARTILE ACCURACY, UPPER QUARTILE ACCURACY, AND THE AREA UNDER THE RECEIVER OPERATING CURVE. THE TOP ACCURACY AND AUC ARE IN BOLD.

TABLE XXI

| Classifier | Features | # | Avg Accy | LQ Accy | UQ Accy | AUC |
|---|---|---|---|---|---|---|
| Decision Tree | Volume | 1 | 45% | 40% | 50% | 0.45 |
| Rules | Volume | 1 | 32.5% | 45% | 20% | 0.223 |
| Naive Bayes | Volume | 1 | 45% | 60% | 30% | 0.388 |
| SVM | Volume | 1 | 15% | 20% | 10% | 0.15 |

SURVIVAL LEAVE-ONE-OUT ACCURACY RESULTS USING ONLY VOLUME CONTAINING THE FEATURE SELECTION METHOD, NUMBER OF FEATURES, AVERAGE ACCURACY, LOWER QUARTILE ACCURACY, UPPER QUARTILE ACCURACY, AND THE AREA UNDER THE RECEIVER OPERATING CURVE. THE TOP ACCURACY AND AUC ARE IN BOLD

Methods—Quantitative Feature Selection

Classically, CT imaging is routinely used to establish anatomical and macroscopic pathologies in cancer patients. Although not commonly used, CT images of tumors also depict characteristics that can be related to physiological processes, such as cell density, necrosis and perfusion. The appearance of the tumor in CT images has been used, qualitatively, to provide information about tumor type, degree of spread and organ invasion. Such features are typically described subjectively (e.g. "mildly irregular", "highly spiculated", "moderate necrosis"). However, to be useful as biomarkers, features must be reproducible, quantifiable and objective. Thus, there is a need to identify features from CT images that can be reliably extracted and converted into quantifiable, mineable data as potential prognostic, predictive or response biomarkers. In current clinical practice, only two tumor quantitative CT features—bi- and uni-dimensional measurements (WHO and RECIST, respectively) are routinely obtained and used to assess response to therapy. While these are satisfactory under some conditions, reduction in tumor size often does not reflect clinico-pathological response.

Recent advances in both image acquisition and image analysis techniques allow semi-automated segmentation, extraction and quantization of numerous features from images, such as texture. Such features extracted from CT images of lung tumors have been shown to relate to glucose metabolism and stage, distinguish benign from malignant tumors, or differentiate between aggressive and nonaggressive malignant lung tumors. In liver cancer, combinations of twenty-eight image features obtained from CT images could reconstruct 78% of the global gene expression profiles. As this area of investigation continues to expand, a number of critical questions remain unanswered, including the redundancy and reproducibility of individual features. In the present study, a large number of image features describing shape, size, run length encodings, attenuation histograms, textures, entropy, and wavelets are extracted and analyzed. In this agnostic approach, equal importance is given to all features with no prior bias towards radiologist preferences or accepted semantics. Such an analysis of a high dimensional feature space, i.e. "radiomics", requires standardization and optimization to qualify these potential biomarkers for prognosis, prediction or therapy response. An important step in the qualification process is to statistically characterize individual features as being reproducible, non-redundant and having a large biological range. The most reproducible features are more likely to be able to identify subtle changes with time, pathophysiology or in response to therapy. Additionally, the reproducibility must be compared to the entire biological range available to that feature across patients. The biological range relative to reproducibility can be expressed as a dynamic range (DR). It is expected that features will be more useful if they have a large dynamic range. In addition, features must be identified that are not redundant, as it is axiomatic that redundant features can overwhelm clustering algorithms and decision support systems.

The inter-scan reproducibility of features may be affected by differences in patient variables, such as positioning, respiration phase and contrast enhancement, as well as acquisition and processing parameters, including image acquisition power and slice thickness, image reconstruction algorithm, segmentation software and user input for segmentation. In the present study, the acquisition and processing parameters were fixed, and patient variables were minimized by obtaining two separate CT scans from the same patient on the same machine using the same parameters, within 15 minutes of each other. Acquisition of these images and reproducibility of tumor uni-dimensional, bi-dimensional and volumetric measurements has been previously reported. These data have been made publically available under the NCI-sponsored Reference Imaging Database to Evaluate Response (RIDER) project. The objective of the current study is to determine the variability in a large set of agnostic image features from this data set in order to identify the most informative features using empirical filters.

In prior work, it was demonstrated that semi-automatic (e.g., Manual) segmentation had 73% overlap between operators across a test set of 129 patients. Hence, lesions in the current study were segmented and 219 features were extracted from these segmented volumes. The feature set covers a broad range of shape, size, and texture type features.

Although the study began with a large feature set compared to prior conventional radiological analyses, it is expected that there may be redundancy in these features due to the sample size and the fact that a number are in the same family (e.g., texture). Thus, to reduce the dimensionality of this agnostic data set, features were first filtered based on their reproducibility, e.g., those with the highest intra-feature concordance correlation coefficients (CCC) between the repeats. As a second filter, dynamic range based on inter-patient variability was used. Finally, redundancy was assessed by computing an inter-feature coefficient of determination ($R^2_{Bet}$) between all possible pairs of features. A representative feature set was found by combing dependent groups to form an independent set. These features could also be used for prognosis prediction or prediction of progression or other analysis, a practical application is also provided.

Data Collection

In brief, baseline and follow up CTs of the thorax for each patient were acquired within 15 minutes of each other (e.g., the fixed time period as used herein), using the same CT scanner and imaging protocol. It should be understood that a fixed time period of 15 minutes is used only as an example and that fixed time periods more or less than 15 minutes can be used. Among other possibilities, this enables testing extracted image features for stability. Unenhanced thoracic CT images were acquired using 16-detector (GE Light-Speed) or 64-detector (VCT; GE Heathcare) scanners, with 120 kvp tube voltage and image slices thickness of 1.25 mm were reconstructed using the same lung convolution kernel without overlap. The CT scans were acquired from 32 patients (mean age, 62.1 years; range, 29-82 years) with non-small cell lung cancer. There were 16 men (mean age, 61.8 years; range, 29-79 years) and 16 women (mean age, 62.4 years; range, 45-82 years). All patients had a primary pulmonary tumor of 1 cm or larger. These images were deposited in the National Biomedical Imaging Archive (NBIA) maintained by NIH. The images are available in the "RIDER Lung CT" collection in NBIA under the "Collections" sections.

Segmentation of Tumors

DEFINIENS DEVELOPER XD of DEFINIENS AG of MUNICH, GERMANY was used as the image analysis platform. It is based on the COGNITION NETWORK TECHNOLOGY which allows the development and execution of image analysis applications. Here, the Lung Tumor Analysis (LuTA) application was used. LuTA contains a semi-automated three-dimensional click-and-grow approach for segmentation of tumors under the guidance of an operator, hereinafter referred to as "manual" segmentation. The "manual" workflow contained the following steps: (a) Pre-processing: The preprocessing performed automated organ segmentation with the main goal of segmenting the aerated lung with correct identification of the pleural wall in order to facilitate the semi-automated segmentation of juxtapleural lesions. (b) Semi-automated correction of the pulmonary boundary: In order to perform the seed based segmentation of a target lesion, the latter has to be completely within the extracted lung image object. In cases where a medical expert concluded that the automated preprocessing described above failed to accurately identify the border between a target lesion and the pleural wall, it was necessary to enable correction of the automated lung segmentation. To this end, the image analysts identified the part of the lung that needed modification and placed a seed point manually where the segmentation should be corrected. A seed point outside the lung defined a lung extension, whereas a seed point inside the lung defined a reduction. (c) Click and Grow: In order to segment a target lesion the image analysts identified the lesion within the segmented lung and placed a seed point in its interior—typically at the perceived center of the lesion. If the growing process did not sufficiently capture the target lesion, the operator could place additional seed points within the lesion and repeat the growing process outlined above. Upon completion of the segmentation, the individual image objects were merged to form a single image object representing the segmented target lesion. (d) Manual refinement and generation of lesion statistics: Upon completing a seed based lesion segmentation as described above; the results were viewed by scrolling up and down the stacks of axial images to verify that the segmentation followed the anatomical compartment boundaries properly. To facilitate manual adjustment of the seed based growing algorithm, tools of two types were constructed. The first type allowed the operator to limit the boundaries beyond which the region could grow during the "Click-Grow" step by manually placing "blocker" points. Another approach allowed for manual editing of the contour of each segmented lesion on each axial slice by cutting, merging and reclassifying objects and thus enabled the image analysts to perform any desired modifications of the segmented lesion. Image analysts were empowered to override as much or as little of the semi-automatically grown regions as their expertise suggested was indicated. The "manual" segmentation (MS) process (a)-(d) above required multiple human interactions in order to get the 'correct' segmentation boundaries.

Once the segmentation of all target lesions was complete, statistics for each lesion, such as volume, center of gravity and average density, all readily available as object features within the commercial cognitive network language (CNL), were extracted. In total, 64 lesions were segmented, i.e. 2 per patient. Then quantitative values of image features were extracted from each segmented volume.

Image Features

Several types of image features were extracted to describe the tumors heterogeneous shape and structure (details in the subsection below). It is to be noted that there are multiple features extracted in some of the categories. As described above, texture features are good descriptors of the tumor and have shown relevance for survival prediction. In this study, 219 custom 3-dimensional image features were used. The features details are described in Tables A1 and A2 above. Most size and shape based feature computation were implemented within the DEFINIENS DEVELOPER XD platform, while texture and other derived features were computed from algorithms implemented in C/C++. All the features were obtained from the region of interest (e.g., after the segmentation).

Feature Categorization

The agnostic features types were assembled to describe the tumor lesion, though 219 features seems like a large set may other effective descriptors may yet need to be added. The feature set is categorized into seven broad categories to describe the lesion, namely: size based, shape based, location based, Pixel histogram intensity based, Run length & Co-occurrence, Law's kernel based texture and Wavelets based texture descriptors. Tables A1 and A2 shows the number of features in each of the categories. The approach has been driven by the conventional radiologist belief that a heterogeneous tumor lesion is best described by an ensemble of factors ranging from tumors' shape, size, location, and density. It has also been shown that features are dependent within and across the categories. The approach is to find representative features in each category so as to "best describe" the tumor in feature space. Comprehensive descriptors to cover most categories have been assembled.

Feature Selection Procedure

The sets of informative features were selected using a three step process. First, the consistency between the Test and Re-Test experiments were tested. For each image feature the concordance correlation coefficient was used to quantify reproducibility between two scans performed on each patient. The Concordance correlation coefficient is superior to the Pearson correlation coefficient for repeated experiments. If $X_{1,k}$ and $X_{2,k}$ are the feature values for $k^{th}$ feature, assuming $(X_{1,k}(i), X_{2,k}(i))$ are independent and follow a bivariate distribution with means and covariance matrix: $\mu_{x1}$, $\mu_{x2}$ and $([\sigma_{x1,k}^2, \sigma_{x1,k, x2,k}^2], [\sigma_{x1,k, x2,k}^2, \sigma_{x2,k}^2])$, for the lesions measured in the $i^{th}$ test and retest experiment. Then the Concordance coefficient (CCC) is given by the following Eqn. (1), $$CCC = \frac{(2\sigma_{x_{1,k},x_{2,k}})}{(\sigma^2_{x_{1,k}} + \sigma^2_{x_{2,k}} + [\mu_{x_{1,k}} - \mu_{x_{2,k}}]^2)} \quad (1)$$

The CCC evaluates the degree to which the experimental samples are located on the 45° line through the origin in a plot spanned by the two measurements $X_{1,k}$ & $X_{2,k}$. The concordance correlation is typically used to measure the deviation in repeated experiments because of its ability to measure deviation from the best fit of the data to the 45° line through the origin. The CCC values ranges from 1 to −1, implying perfect agreement between the repeated experiments to reverse agreement between them.

On this set of highly reproducible features, the next step was to select the features with a large inter-patient variability, using the "dynamic range". The normalized dynamic range for a feature was defined as the inverse of the average difference between measurements divided by the entire range of observed values in the sample set as in Eqn. (2):

$$DR_k = \left(1 - 1/n \sum_{i=1}^{n} \frac{|Test_k(i) - ReTest_k(i)|}{Max_k - Min_k}\right) \quad (2)$$

where i refers to sample index, for the $k^{th}$ feature, $Test_k(i)$ or $ReTest_k(i)$ are sample i's $k^{th}$ feature values for a Test/ReTest population of n patient cases, the maximum ($Max_k$) and minimum ($Min_k$) are computed on the entire sample set. The dynamic range for feature k has a range, $DR_k \in [0,1]$. Values close to 1 are preferred, and imply that the feature has a large biological range relative to reproducibility. Increasing the variation between the Test-Retest repeats will lead to a reduction in the DR value. Screening for a large DR will eliminate features that show greater variability in the repeat scans compared to the range of the coverage. The dynamic range measure will effectively address the 'effect size' by identifying features with a lower value that are either not reproducible (relative to their range), or that are not highly variable across an entire sample set. This metric helps to score features with a higher score for one that shows relatively larger coverage with respect to the repeatable differences, this does not intend to describe the dynamic range of the entire population.

The last step is to eliminate redundancies, based on the calculation of dependencies within the group. The coefficient of determination ($R^2_{Bet}$) between the features that passed a dynamic range threshold to quantify dependency were calculated. It is a linear estimate of the correlation or dependency and has a range of 0 to 1. Values close to 1 would mean that the data points are close to the fitted line (i.e. closer to dependency). The coefficient of determination of simple regression is equal to the square of the Pearson correlation coefficient. Different threshold values for $R^2_{Bet}$ were used to consider each feature as linearly dependent on any other feature(s) in the list. The features that passed the cutoff limit were grouped and replaced by a representative from the group; the one having highest dynamic range. The purpose of this third filter was to eliminate redundancies (and not necessarily identify independence). A range of $R^2_{Bet}$ thresholds were explored. The features category were filtered to find the representative in each category to ensure the final set of features have descriptors from each group. Feature reduction taking all the categories of features together was also carried out.

Prognostic Label

An attending radiologist was used to categorize the RIDER test/retest dataset into two broad prognostic groups using quantitative metrics to score the tumor on a point scale. These parameters included tumor size, differentiation, vascular invasion, margin status (negative vs positive or close margins, which have all been shown to have prognostic value. Five scalable metrics were used, e.g., lobulated margin, size of the tumor lesion, spiculated margin, plueral wall attachment and texture (e.g. ground glass opacity, GGO), as factors to scale the tumor into high risk to moderate risk individuals and used fissure attachment, lymphadenopathy and air bronchogram as a secondary flags to grade the lesions. The score values on the point scale were summarized and standardized to a scale of 0 to 1. The normalized prognostic score over the median value was considered high risk (or poor prognosis) versus the sample below, which would mean relatively lower to moderate risk. Two samples could not be scored reliably using the point scale metric due to disperse lesions. In total four samples were eliminated.

Figure 5:
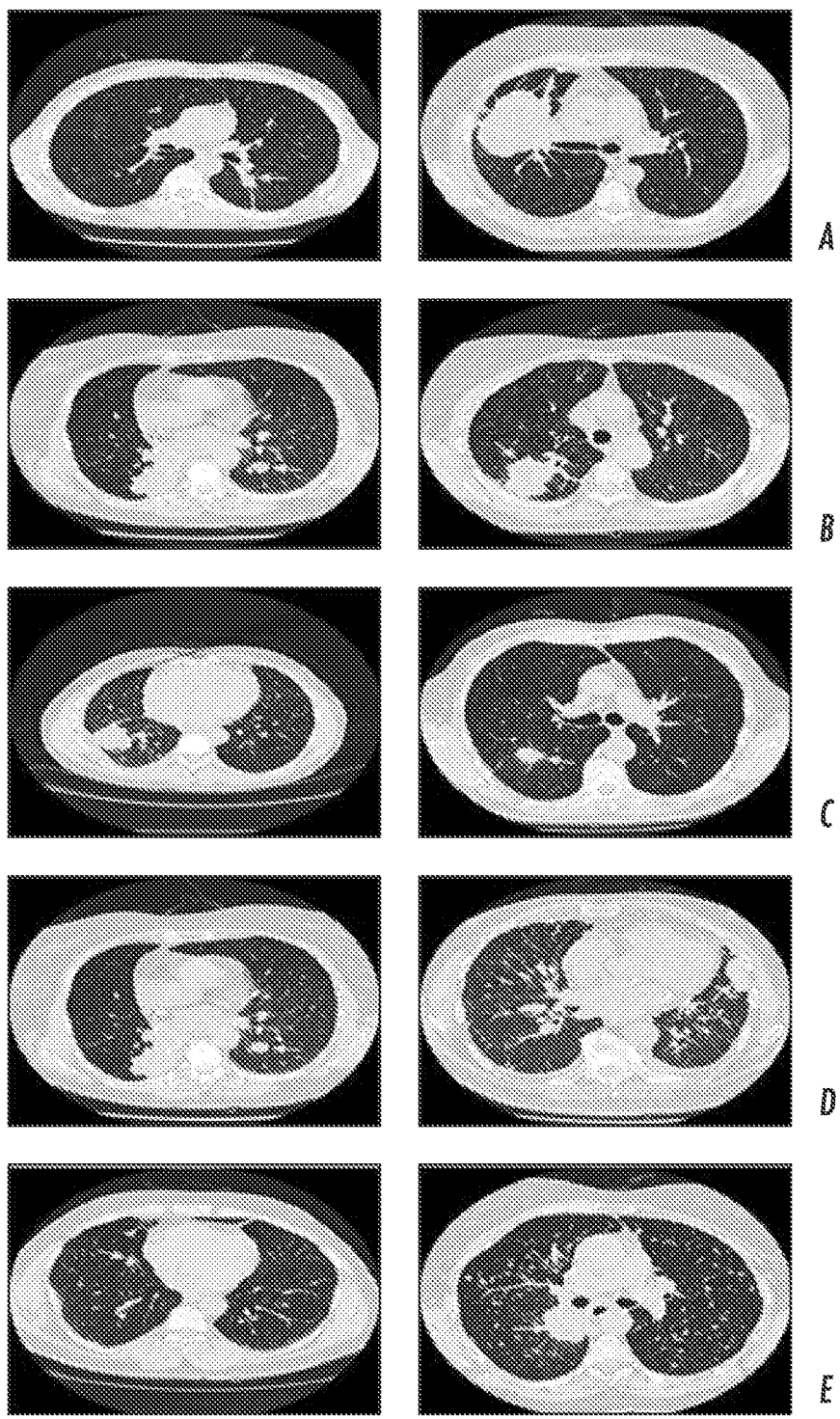
FIG. 5 illustrates examples of CT scans for extreme semantic scores.

These two categories were then used to find discriminatory markers between the poor to better prognosis groups. FIG. 5 illustrates examples of CT scans for extreme semantic scores, wherein the left panel cases represent low scores (e.g., 1 out of 5) and the right panel cases represent high scores (e.g., 5 out of 5).

Feature Selection

The reproducibility of radiographic features obtained from CT scans of lung cancer was investigated to establish potential quantitative imaging biomarkers. Most of the features showed high reproducibility using an automated image analysis program with segmentation done by a single reader. Prior work has demonstrated the use of three features: uni-variate, bivariate and volumetric to infer concordance consistency for automatic and manually segmented lung lesions, which seems to be limited in describing the complex nature of a tumor. In the current study, the focus has been to describe the tumor with many features using different categories: size (volume, diameter, border length), shape (shape index, compactness, asymmetry), boundary region (border length, spiculation), relation to the lung field, image intensity based features (mean, standard deviation, average air space, deviation of airspace, energy, entropy, skewness etc.) and transformed texture descriptors (wavelet transform: entropy and energy and laws features). On this set of features, their consistency in repeat scans (test, re-test) was tested and filtered to find independent features. The stable, independent features provide an image feature set that may, for example, be used to predict prognosis.

One requirement for an image feature to be qualified as a response biomarker is that the change in its value between pre- and post-therapy scans must be significantly greater than the difference observed in the present "Test-Retest" (or "15 minute coffee break") measurements. In the present study, the change of individual features that may be encountered post-therapy to be within the entire pre-therapy biological range can be estimated. The ratio of the range to the inter-scan variability is a measure of "dynamic range. Features showing high dynamic range were considered potentially more informative. The distribution of concordance coefficients between Test and Re-test, which is skewed toward higher end values as one would expect showing high concordance between the Test and Re-Test cases. There is also a larger peak toward zero values, investigating the peaks shows some of the Laws and higher level wavelet features have low concordance between Test, Re-Test repeats. It is hypothesized that the reimaging of the patients resulted in some change in texture (perhaps from segmentation differences). These Laws features compute energy after filtering in a region, small changes in sub regional textures would make these features vary as they capture small localized changes. A similar analogy could be made for wavelet features for higher layer decompositions (or higher layers), where discordance can be seen.

In prior work, a correlation coefficient threshold of 0.9 was used to distinguish highly correlated features. In the current study, the coefficient of determination ($R^2$) was used between the features to find the dependency. It was shown the coefficient of determination in simple linear regression is equal to the square of the Pearson correlation coefficient.

Feature Reduction

Feature reduction to select an informative feature set is an active research field, metrics that have been used in the past, include: the correlation coefficient, regression methods and classification accuracy. In this study, a representative feature set that will eliminate redundancy in terms of information content is intended to be identified, as complete independence may not be relevant for the study as texture information is subjective (and affected by sample issues, scanner setting, protocol followed, etc.). The coefficient of determination ($R^2_{Bet}$) between two features, to form a matrix of all possible pairs to quantify dependency can be used. Features were grouped based on $R^2_{Bet}$ between them (over a certain limit); in this subset one representative was picked that had the highest dynamic range. The procedure was repeated recursively to cover all the features resulting in a most representative group, done independently for each category.

The test, retest values were averaged before computing $R^2_{Bet}$. Different limits were set to combine the features, $R^2_{Bet}$ from 0.75 to 0.99. For higher thresholds $R^2_{Bet}$, less features will be grouped together resulting in a larger representative group. Setting the $R^2_{Bet}$ to a lower limit will group more features together resulting in a smaller representative feature set (i.e. set of independent features). The combination of reproducibility, plus informative and independent sets of features is critical to obtain a feature set which may contain imaging biomarkers. A number of representative features obtained at different thresholds for concordance and dynamic range. As an example, selecting the midlevel threshold $CCC_{TreT}$ & DR≥0.90 yielded 66 features. In this subset, the representative features were found with $R^2_{Bet}$≥0.95 resulting in 42 features.

Figure 6:
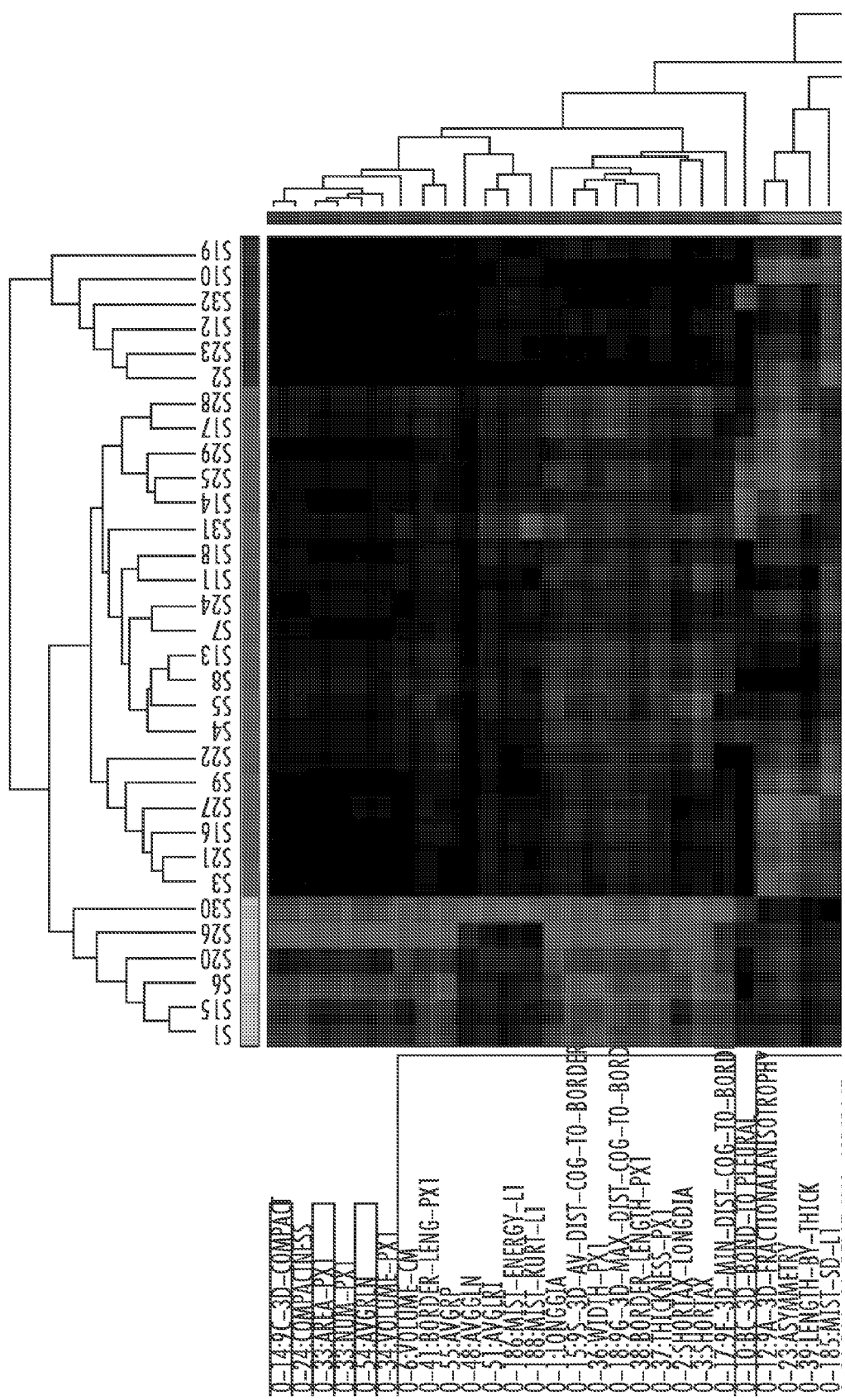
FIG. 6 illustrates a heatmap of coefficient of determination between features.
Figure 6:
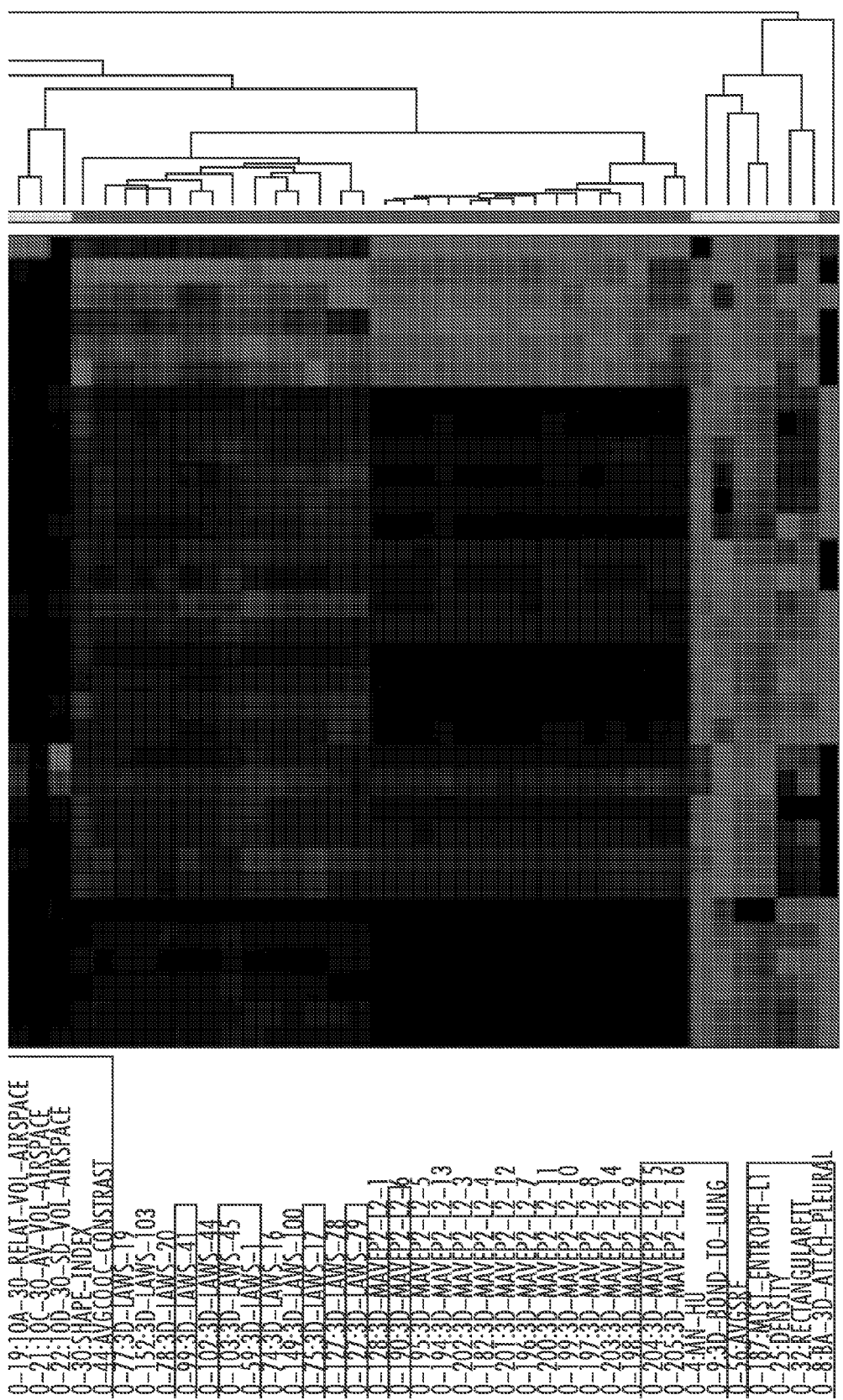

FIG. 6 shows a heatmap of coefficient of determination (R2Bet) between the features, for CCCTreT & DR≥0.90. The features (in the rows) reported are the ones with CCCTreT & Dynamic Range (DR)≥0.90. The features that have been picked as representative features with $R^2$ value≥0.95 are outlined with a solid box. The representative features were picked category wise, displayed across all categories. The hierarchical clustering was stopped arbitrarily at six groups of features and three groups on the sample side, represented by the multicolor bar. The dendograms on the top and sides show complete groupings with average linkage. The color map of the clustogram ranges from 0 to 1, values close to 1 have a red shade and values close to 0 have a black shade. The groups with red shade mean relatively high feature values.

The image features left out of the representative reduced feature set could also be useful features. The image features are expected to capture different aspects of morphology, and texture information. Due to the consistency in samples chosen and a limited sample population the image features computed may show a higher level of dependency. The samples chosen as primary lung tumor may have a limited amount of texture or morphological changes.

Results and Discussion

In the obtained regions of interest (ROI), 219 3D features were extracted, which are described in Tables A1 and A2. The feature names were abbreviated to fit them in the table format, for example: 'F78:3D-Laws-20' would mean, Feature#78 (from the total of 219 features), it's a 3D texture feature, computed by the "Laws" kernel of type 20. The kernel reference can be found in the parenthesis, i.e., 'E5 S5 W5 Layer 1'. All features can be decoded in this way.

Conventional Radiologist Measures:

In order to be comparable with previous work, the concordance correlation confidence limits for segmentation on three features were compared. As before, high concordance across test-retest was found. The difference distribution between test and retest for the three measures (Length, Area, and Volume) were observed. As the tumor size increased, the difference between test & retest was reduced, as observed in previous analyses.

Concordance in the New Features:

The 219 extracted features were first compared using the Concordance Correlation Coefficient, which is a stringent measure of reproducibility. A $CCC_{TreT}$ value≥0.75 indicates that the data are of acceptable reproducibility. For the data set, various thresholds were examined with a preference for high stringency. These analyses identified 45, 66 and 93 features that had CCCTreT values above thresholds of 0.95; 0.90 and 0.85, respectively.

Dynamic Range in New Features:

At a second level of analysis, the dynamic range was computed as described in Methods, and is a measure of biological range for each feature, relative to its reproducibility. Features with a dynamic range≥0.95 have a biological range that is more than 20-fold greater than the test-retest difference. These analyses identified e 59, 189 & 219 feature above dynamic range thresholds of 0.9, 0.90 & 0.85, respectively. Applying both the filters features were identified that passed the threshold set by CCC as well as the Dynamic range filter. These two filtering procedures will result in a set of features that is reproducible and has a large range compared to the variability between the test and re-test experiments.

Redundancy Reduction:

It is known that agnostic features may be inter-dependent. To reduce redundancies, the coefficient of determination ($R^2_{Bet}$) between all possible pairwise combinations of features was used to quantify the level of similarity. In this approach, if a feature of interest is linearly predicted by any other feature in the filtered feature set, then the feature having the largest dynamic range was chosen as the representative for the group and the other was removed. The procedure was repeated to cover the entire subset to form the reduced set. The threshold level to flag features as linearly dependent is critical and is subject to change with the sample size and the tumor shape and texture. Using an $R^2_{Bet}$ threshold of ≥0.95 to identify interdependence, there were 42 features that had CCCTreT & DR values≥0.90. At a lower setting, of $CCC_{TreT}$ & DR≥0.85, there were 53 features.

Practical Application of Repeatable Markers

Quantitative image features have been shown to predict prognosis in prior studies. The objective in this work is to find reproducible, non-redundant and high dynamic range image features that could be prognostic or response markers. Following is a practical example to illustrate the potential utility of these markers, where reproducibility is a required trait for them to be used as a prognostic predictor.

Prognosis Discrimination:

As an application the features that pass the concordance and dynamic range filters were used to test their ability to discriminate groups based on their prognostic score, determined as described in methods. The section below describes details on the sample label information. Statistical tests (T test and Wilcox rank test) were applied to find discriminating image feature between the prognostic groups. The P-values for the features were obtained and the values corrected for multiple testing by computing the false discovery rate (FDR) for the features, performed independently for features in each category. Because they were reproducible, the feature values for the test and retest were taken as independent observations. The features that had a FDR for both tests of 0.05 were considered to be prognostic discriminators.

The sample set was diverse with more large tumors than small ones, and hence most size based features were near the top of the prognostic predictor list. Size is a well-known prognostic feature for many tumors. In addition, it was also observed that a large number of texture features (Histogram, Laws and wavelets) were prognostic. Notably, texture, size & shape based descriptors showed equal prognostic value.

Optimal Threshold:

Linear discriminant analysis was used to find a cutoff level for the significant features. Using the prognostic labels as ground truth sensitivity, specificity and area under the curve (AUC) were computed. Some of the texture features (Runlength, Laws & Wavelets) had to be linearly scaled (by a factor of 1000) before computation to avoid numerical errors.

Figure 7A:
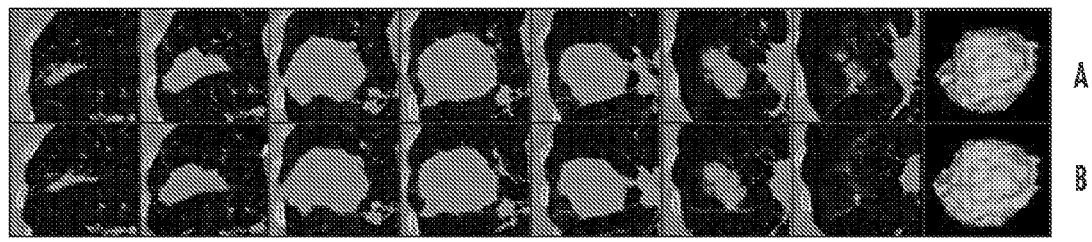
FIGS. 7A and 7B illustrate a receiver operator characteristics (ROC) for two features.
Figure 7A:
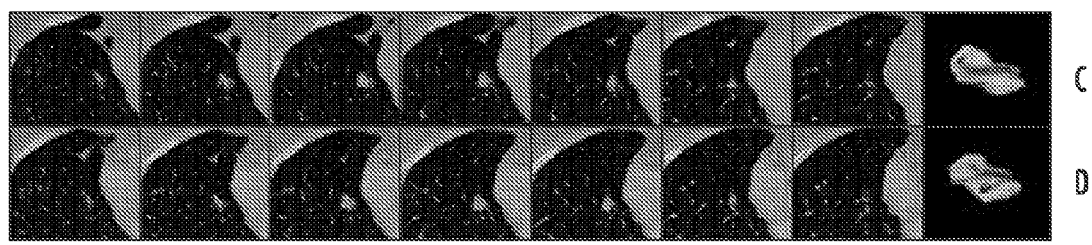
Figure 7B:
Figure 7B:
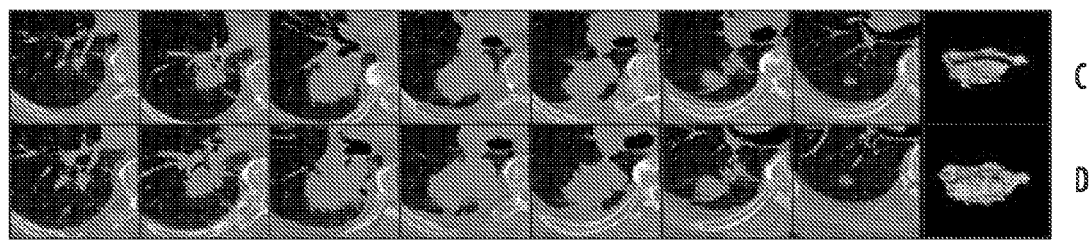

The ROC (receiver operator characteristics) for two features is shown in FIGS. 7A and 7B, the area under the curve is 90% for the conventional size based feature (longest diameter) and 91% for the chosen texture (Run length) feature. Scores were arbitrarily assigned, where below the median as "good" (in green) and those above the median as "bad" (in red), in a relative sense. Segmented region for representative slices from top to bottom of the tumor, for samples with extreme values of texture features (also identified to be predictive of prognostic score). The samples in Case 1, FIG. 7A: (a), (b) & (c), (d) had the highest and lowest Average Run length (F54: Avg.Run.L) measure for test/retest. The feature value for images in (a), (b) was 22153.85 & 221262.36. While (c), (d) was: 688.56 & 700.96 respectively. The samples in Case 2, FIG. 7B: (a), (b) & (c), (d) had the highest and lowest laws kernel measure (F59: Laws −1: E5 E5 E5 Layer 1) for test/retest. The feature value for images in (a), (b) was 0.07404 & 0.07507. While (c), (d) was 0.00864 & 0.00658 respectively.

Figure 8A:
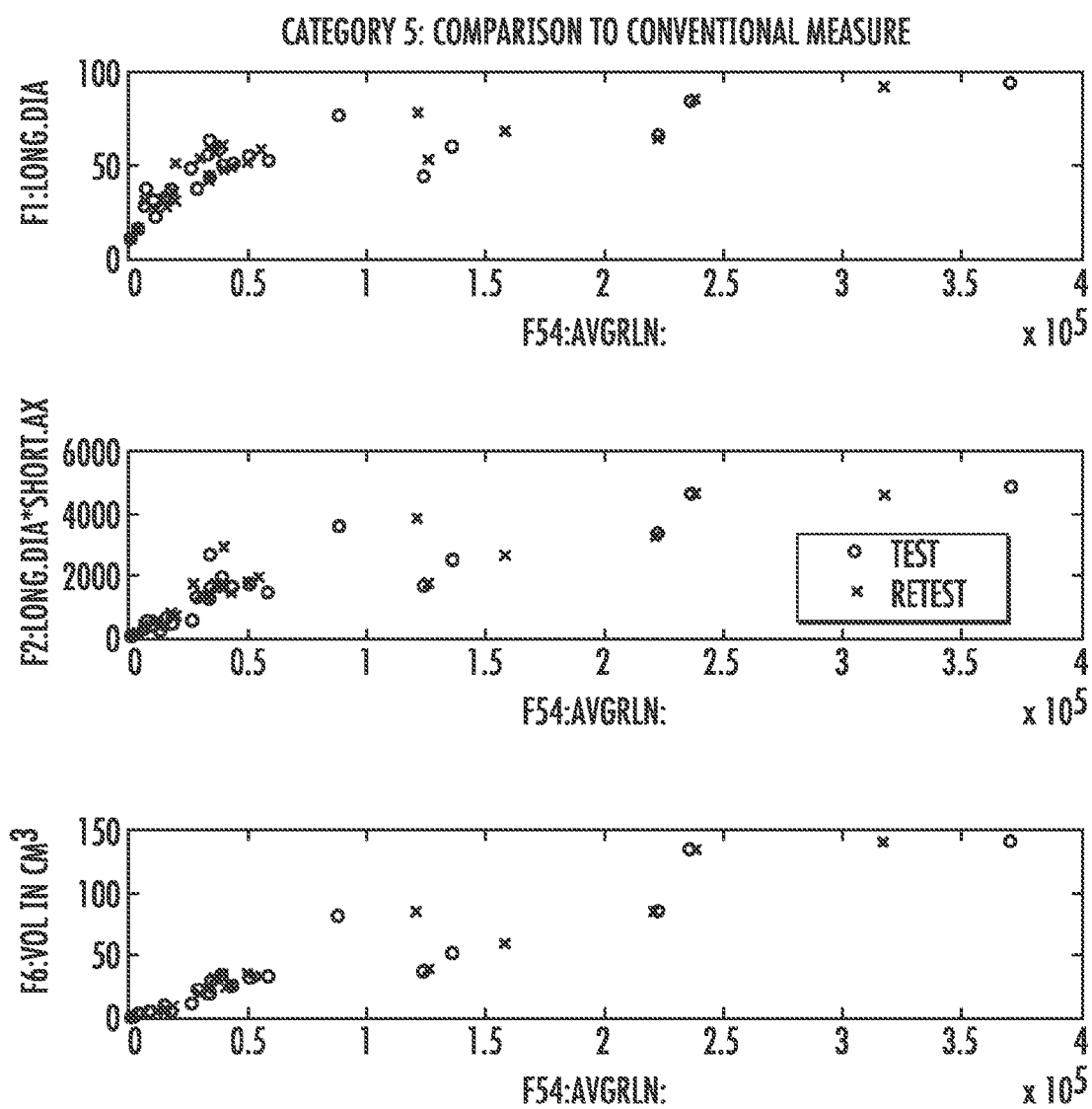
FIGS. 8A and 8B illustrate two sample cases with representative slices for Run length and a Laws kernel.
Figure 8B:
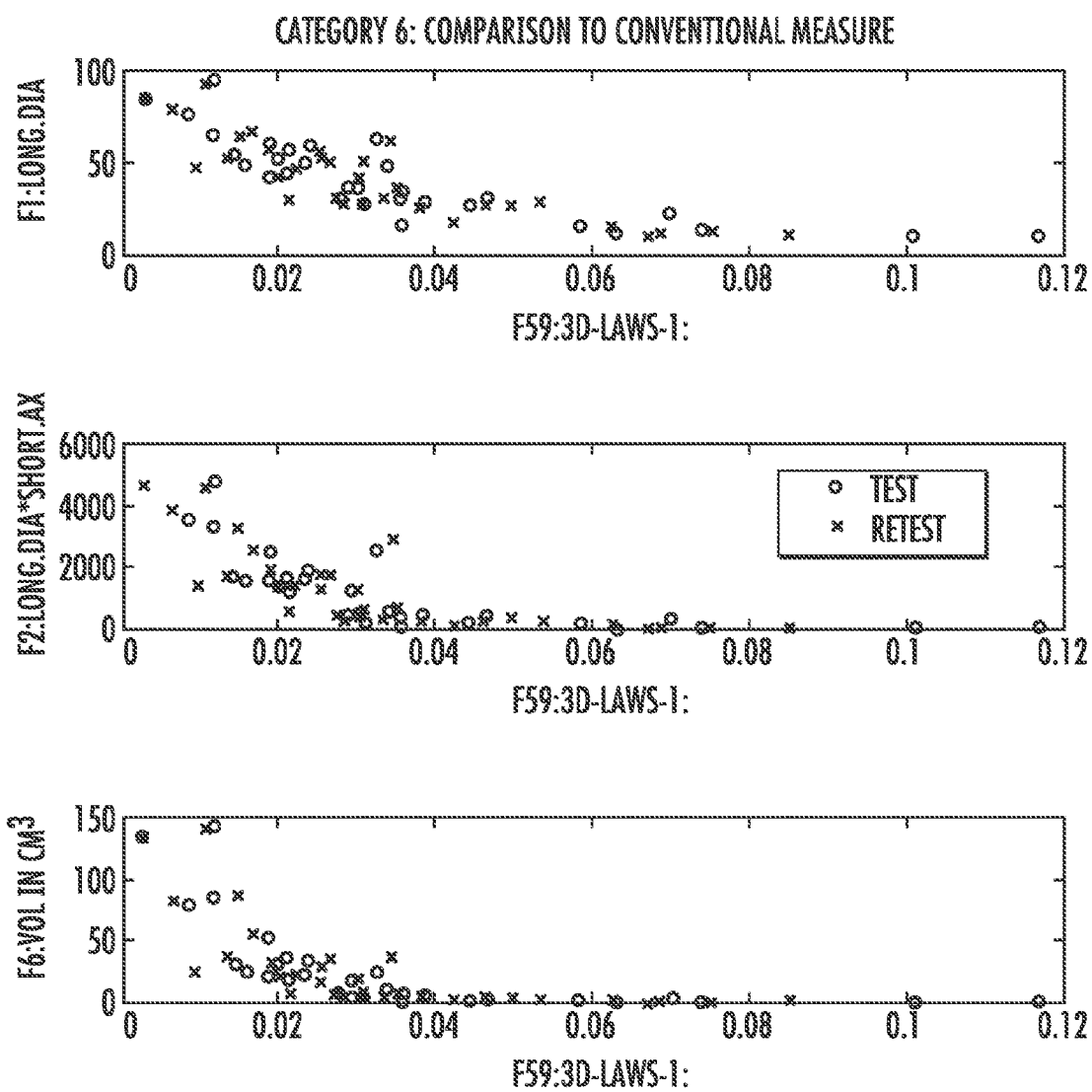
Figure 9:
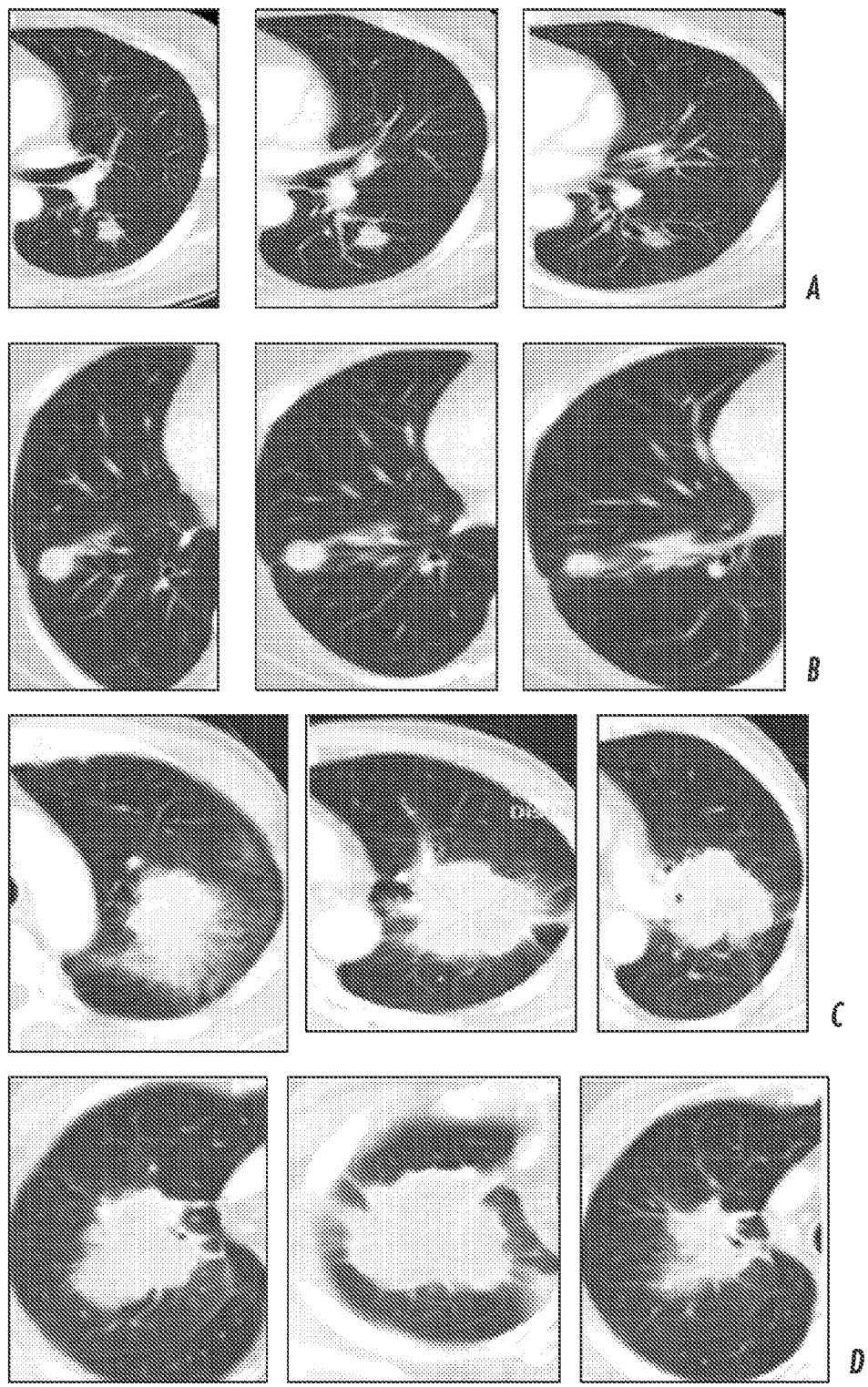
FIG. 9 illustrates the relationship of prognostic texture features to conventional measures.

The example in FIGS. 8A and 8B show two extreme sample cases with representative slices for Run length and a Laws kernel feature. FIGS. 8A and 8B show prognostic texture features relationship to conventional measures (Longest Axis, Short Axis*Longest Axis & Volume). In particular, FIG. 8A shows run length features and FIG. 8B shows Laws kernel features. The Laws 1 (E5 E5 E5 Layer 1) is an edge detecting kernel of length 5, applied across all directions (x, y & z) and normalized based on the size of the tumor. It is expected to have an inverse relation to tumor size and expected to measure tumors edges. FIG. 9 shows the relationship of the prognostic feature to the conventional measures. It shows in the lower range it tracks the size measurement but deviates as the feature value increases. These texture features may capture more information than traditional size based measurements. In particular, FIG. 9 shows three representative slices of patient CT scans selected from 39 Adenocarcinoma cases with better radiological prognostic score (A&B, score of 0.44 & 0.48 respectively) and poor radiological prognostic score (C &D, score of 0.8, 0.92 respectively).

Conclusions

The current study demonstrates that the test-retest reproducibility of most CT features of primary lung cancer is high when using an image analysis program with semi-automated segmentation. Across all patients, the biological ranges for the majority of individual features were very high. The features with lowest inter-scan variance relative to the largest biological range (i.e. dynamic range, DR) should be explored as potentially the most informative for use as imaging biomarkers. Additionally, a co-variance matrix of features identified several redundancies in the feature set that could be combined into a single variable. Combining inter-scan variance, biological range and co-variance, it is possible to reduce the total number of features from 219 to a most informative set of 42 features identified at a setting of $CCC_{TreT}$ & DR≥0.9 ($R^2_{Bet}$≥0.95), while a less stringent cutoff there are 77 features with $CCC_{TreT}$ & DR≥0.85 ($R^2_{Bet}$≥0.99). These reproducible and representative features show high ability to discriminate the tumors based on its prognostic labels. There were 69% of size based features, 62% of histogram features and 29% Run length features were able to discriminate tumors with low and high prognostic scores. This allows selection of reproducible, informative and independent features that are candidate imaging biomarkers to predict prognosis and predict or assess therapy response.

Lexicon Development of Quantitative Computer Tomographic Characteristics for Lung Adenocarcinoma and Their Association With Lung Cancer Survival As described below, 25 CT descriptors have been developed from among 117 patients with lung adenocarcinoma and found that, of these, pleural attachment was most significantly associated with an increased risk of death overall and among patients with adenocarcinomas showing pure lepidic growth or with lepidic growth as its predominant component, while lymphadenopathy was significantly associated with an increased risk of death among patients with adenocarcinomas without a predominantly lepidic component. An initial set of CT descriptors was developed to quantitatively assess lung adenocarcinomas in patients (n=117) who underwent resection. Survival analyses were used to determine the association between each characteristic and overall survival. Principle component analysis (PCA) was used to determine characteristics that may differentiate histological subtypes.

The twenty-five descriptors were developed using either an ordinal scale from 1 to 5 or binary categorical rating. Characteristics significantly associated with overall survival included pleural attachment (P<0.001), air bronchogram (P=0.03), and lymphadenopathy (P=0.02). Multivariate analyses revealed pleural attachment was significantly associated with an increased risk of death overall (Hazard Ratio [HR]=3.42; 95% confidence interval [CI] 1.70-6.86) and among patients with adenocarcinomas showing pure lepidic growth or with lepidic growth as its predominant component (HR=5.98; 95% CI 1.78-20.16), while lymphadenopathy was significantly associated with an increased risk of death among patients with adenocarcinomas without a predominantly lepidic component (HR=2.90; 95% CI 1.08-7.80). A PCA model showed that tumors with or without predominant lepidic growth were separable and texture was most important for separating the two subtypes.

As described below, a standardized set of quantitative computer tomographic (CT) descriptors of lung adenocarcinoma has been developed and their association with overall survival assessed. This approach has the potential to support automated analyses by providing guidance and expert evaluation of necessary imaging characteristics, and it can ultimately be used to develop decision support clinical tools to increase accuracy and efficiency of radiological diagnosis.

A study included 117 patients diagnosed with histologically confirmed adenocarcinoma of the lung who had surgery for primary lung cancer between January 2006 and June 2009. Tumors were further classified into two subtypes: (1) Bronchioloalveolar carcinoma (BAC) and adenocarcinoma with a predominant BAC component, and (2) Adenocarcinoma without a predominant BAC component. Since the BAC classification is no longer used, the histopathologic term "lepidic" has been introduced to describe the pattern of adenocarcinomas that possess growth along the surface of alveolar walls. For this analysis the tumors are classified into two groups: group 1: adenocarcinoma with evidence of pure lepidic growth or with lepidic growth as its predominant component; and group 2: adenocarcinoma without a predominant lepidic growth.

All CT scans were performed prior to surgery. Slice thicknesses varied between 3 to 6 mm (n=18 with 3 mm, n=24 with 4 mm, n=74 with 5 mm, and n=1 with 6 mm). Ninety-five patients underwent contrast-enhanced CT and 22 patients had non-enhanced CT. A clinical radiologist with 7 years of experience in chest CT diagnosis read all of the CT images and developed the descriptors. Terms and descriptions were adapted from the Breast Imaging Reporting and Data System (BI-RADS) of the American College of Radiology. Lung cancer-specific characteristics are included from the Fleischner Society and those that have been previously published. Each descriptor was rated with either an ordinal scale from 1 to 5 or rated as a binary (present or not present) categorical variable. Each tumor was rated by assessing all slices and reporting with a standardized scoring sheet. Intentionally, the ordinal scale was broadened with the potential to collapse the resolution as evidence is obtained.

Kaplan-Meir survival curves with the log-rank test were performed using R version 2.14 (R Project for Statistical Computing, http://www.r-project.org) and multivariable Cox proportional hazard regression was performed using Stata/MP 12.1 (StataCorp LP, College Station, Tex.). Among characteristics that were found to be statistically significantly associated with overall survival in univariate analyses, forward selection methods were utilized to model which sets of CT characteristics were associated with overall survival. Also performed was a Classification and Regression Tree (CART) adapted for failure time data that used the martingale residuals of a Cox model to approximate chi-square values for all possible cut-points for the characteristics (http://econpapers.repec.org/software/bocbocode/s456776.htm). Principle component analysis (PCA) was used to determine characteristics that may differentiate histological subtypes.

Results

CT descriptors and patient cohort: Twenty-five descriptors were developed and used to evaluate lung CT scans from patients with lung adenocarcinomas. The goal was to develop an initial set of descriptors covering a broad area of characteristics with as much resolution as possible. As shown in Table 22, these descriptors were classified into three categories: (1) measures describing the tumor (n=16); (2) measures describing the surrounding tissue (n=5); and (3) measures describing associated findings (n=4). Among these descriptors, 17 were rated using a 1-5 ordinal scale and 8 descriptors were binary categorical variables. Fifty-five tumors were classified as group 1, showing pure lepidic growth or with lepidic growth as its predominant component; 62 tumors were classified as group 2, without a predominant lepidic growth and, among these cases, 11 had a small proportion of a lepidic component.

Comparison of lung-tumor descriptors with existing classification systems: The set of descriptors was adapted in part from those described in the BI-RADS lexicon (10, 14). Because a goal was to quantitatively describe characteristics within CT lung images with an ordinal scale when applicable, the measures do not parallel exactly the related descriptions defined in the BI-RADS lexicon. For the shape of the tumor, degrees of sphericity was used to describe the roundness, whereas the BI-RADS uses two shapes (i.e., round or oval). For the margin description degrees of border definition was used, whereas the BI-RADS uses circumscribed (well-defined or sharply-defined) or indistinct (ill-defined); and fissure or pleural attachment was used to indicate the obscured margin used by BI-RADS (Table 23). For the density of the tumor, the descriptors were quite different from BI-RADS descriptors due to the difference between the two organs; focus was on the ground-glass opacity (GGO) and used the lexicon of the Fleischner Society for reference. Calcification is a separate category of BI-RADS and there are many terms used to describe it because calcification is very important for breast imaging to infer malignancy. However, calcification is rare in lung adenocarcinomas, so it was incorporated into the density description. Similar to BI-RADS MRI, the enhancement heterogeneity of the tumor was described, but with 5 scales. In addition, some specific terms were added used for lung cancer only (Table 22).

The descriptors were developed specifically for patients with pathologically confirmed lung cancer, which is in contrast with many of features defined in the Fleischner Society's glossary. The Fleischner Society terms are used for thoracic imaging in general, although the density descriptors were adapted. Other descriptors that were not included in the lexicon of Fleischner Society were adapted from the literature. In particular, "cavity" and "pseudocavity" used by Fleischner Society was combined into "air space" as Matsuki et al did because of the difficulty to differentiate them on CT images.

Quantitative CT characteristics and overall survival: CT imaging data were available on 117 patients (Table 24) but complete survival data were only available for 105 patients, with 50 patients in group 1 and 55 patients in group 2. First was analyzed the association of CT scanning parameters with the overall survival. The slice thickness (P=0.70) was not associated with overall survival, although the contrast enhancement status (P=0.06) trends towards differences. This result suggests that technical factors do not play a large role in the prognostic ability of the image features. Based on the distributions in Table 24, the association of each of the 25 characteristics was analyzed with overall survival. The characteristics statistically significantly associated with overall survival (FIG. 1) were pleural attachment (P<0.001), air bronchogram (P=0.03), and lymphadenopathy (P=0.02). Size, lobulation, and thickened adjacent bronchovascular bundle are also associated with overall survival (P<0.05), yet these results may be influenced by small sample sizes.

As shown in Table 25, for the multivariable Cox proportional hazard models, the main effects for pleural attachment were first determined, air bronchogram, and lymphadenopathy, and then stratified the data by group. Pleural attachment (Hazard Ratio [HR]=3.42; 95% confidence interval [CI] 1.70-6.86) was statistically significantly associated with an increased risk of death among all patients and among group 1 tumors (HR=5.98; 95% CI 1.78-20.16). For group 2 patients, lymphadenopathy was associated with an increased risk of death (HR=2.90; 95% CI 1.08-7.80). A forward stepwise selection approach revealed similar findings. A CART analysis was performed for pleural attachment, air bronchogram, and lymphadenopathy, and it was found that patients without pleural attachment and without lymphadenopathy had significantly improved survival compared to patients with pleural attachment (P<0.001).

Difference between the characteristics of histological subtypes: PCA analysis of the imaging characteristics demonstrated that the two subtypes (adenocarcinoma showing pure lepidic growth or with lepidic growth as its predominant component and adenocarcinoma without a predominant lepidic growth) were separable. The PCA model explained 14% and 11% of the variation in components one and two, respectively. The separation of the two subtypes was mostly along the second PCA component, shown on the y-axis. The PCA loading plot showed that texture was most important for separating the two subtypes, where adenocarcinomas showing pure lepidic growth or with lepidic growth as its predominant component tended to have more of a ground-glass appearance, i.e. lower value for the texture characteristic. It is also noteworthy that the surrounding tissues and associated findings were important to the PCA model (their loading values were not zero) and added important information to the tumor characteristics. Interestingly, adenocarcinomas with only a minimal lepidic component also showed some extent of lepidic growth characteristics. Some of the adenocarcinomas belonging to group 2 that were "misclassified" into group 1 are actually adenocarcinomas with a small proportion of a lepidic component.

Thus, of the 25 CT descriptors among 117 patients with lung adenocarcinoma and found that, of these, pleural attachment was most significantly associated with an increased risk of death overall and among patients with adenocarcinomas showing pure lepidic growth or with lepidic growth as its predominant component, while lymphadenopathy was significantly associated with an increased risk of death among patients with adenocarcinomas without a predominantly lepidic component.

BI-RADS is the most widespread standardized reporting system and was developed for breast screening. The BI-RADS model was utilized as the guiding principle to develop the descriptors for lung cancer. The lexicon of the Fleischner Society (11) is well-accepted for thoracic imaging in general, and it was used as a guide for the analyses presented herein. A goal is to develop a lexicon that can support automated analysis in the clinical setting by providing guidance and expert evaluation of important imaging characteristics. In many instances documenting the presence of a given characteristic may be insufficient. For example, previous work used spiculation as one possible margin rating. In contrast, spiculation was used as a variable unto itself with five degrees.

It is recognized that because the previous term BAC included several subcategories of varying histopothologic, radiologic, and prognostic clinical importance, BAC is no longer used according to the new multidisciplinary classification of lung adenocarcinoma sponsored by the International Association for the Study of Lung Cancer, American Thoracic Society, and European Respiratory Society in 2011 (15). BAC was a focus because the 2004 WHO lung cancer classification was used as criterion when the patients underwent surgery, and adenocarcinoma showing lepidic growth does have unique clinical and radiological features. Moreover, BAC is a designation that has been used for over 50 years, the problems remaining with the newly developed classification were pointed out by some pathologists and whether BAC can really disappear from the lexicon has been questioned.

BAC was defined as an adenocarcinoma with pure lepidic growth without invasion of stromal, blood vessels, or pleura. Due to its specific growth pattern, BAC usually has unique clinical and radiological features. Many investigators have reported a correlation between histopathologic and CT findings in adenocarcinomas. BAC and adenocarcinoma with a predominant BAC component typically show GGO on CT, which reflects the lepidic growth pattern involving alveolar septa with a relative lack of acinar filling. It is generally accepted that during the progression from BAC to invasive adenocarcinoma, a GGO nodule increases in size, after which the solid portion tends to appear, finally, the solid portion increases in extent. The study analyzed the quantitative CT characteristics of adenocarcinomas by using PCA modeling and found adenocarcinoma showing pure lepidic growth or with lepidic growth as its predominant component can be separated from adenocarcinoma without a predominant lepidic growth, and the most important characteristic that differentiated those two subtypes is texture. This result conforms to the progression of BAC. Analyzed further is the adenocarcinomas without a predominant lepidic growth and it was interesting that adenocarcinomas with only minimal lepidic component also showed some extent of lepidic growth characteristics. These results suggest quantitative CT characteristics can be used to predict histological subtypes of adenocarcinoma based on lepidic component.

Some reports have shown prognostic factors of lung adenocarcinoma from CT findings (19, 23, 24). Smaller extent of GGO, lack of lobulation or air bronchograms, presence of coarse spiculation, and thickening of bronchovascular bundles around the tumors were correlated with poorer survival, which were similar to these results. A relationship between extent of GGO with survival was not observed. As this relationship was reported to be found in small (<3 cm) tumors (19, 23, 24), it should be investigated further. In particular, pleural attachment was found to be the most important characteristics correlated with overall survival, especially for adenocarcinoma showing pure lepidic growth or with lepidic growth as its predominant component. In addition, the prognostic factors for adenocarcinoma showing pure lepidic growth or with lepidic growth as its predominant component were found to be different from those for adenocarcinoma without a predominant lepidic growth. This suggests that the different histological subtypes of adenocarcinoma based on lepidic component should be analyzed separately when quantitative CT characteristics are assessed for their association with lung cancer outcomes.

There is increased interest and awareness in quantitative imaging, particularly in the context of automated CT image analysis. This lexicon provides a standard against which quantitative imaging features may be designed and compared. Further, a goal was to enumerate as broad a descriptor set as possible. This would provide the opportunity for analytical techniques to be designed to detect features or characteristics not detectable by the human eyes. Such features can easily be compared against the lexicon of the present disclosure to demonstrate their uniqueness with respect to radiological observations.

In conclusion, the initial results of the study show that quantitative CT characteristics were associated with overall survival in a cohort of lung adenocarcinoma patients. Specifically, pleural attachment was associated with an increased risk of death, especially among adenocarcinomas showing pure lepidic growth or with lepidic growth as its predominant component. The retrievable data elements in the quantitative CT characteristics can be used for data mining and developing automated objective features, which would benefit therapy planning and ultimately improve patient care.

TABLE 22

Lexicon of CT characteristics for lung adenocarcinoma

| Characteristic | Definition | Scoring | Scoring definition |
|---|---|---|---|
| Tumor Space Localization | | | |
| Location | Lobe location of the tumor | 1, 2, 3, 4, 5 | 1-right upper lobe; 2-right middle lobe; 3-right lower lobe; 4-left upper lobe; 5-left lower lobe |
| Distribution | Central location: tumor located in the segmental or more proximal bronchi Peripheral location: tumor located in the subsegmental bronchi or more distal airway | 0, 1 | 0-central; 1-peripheral |
| Fissure attachment | tumor attaches to the fissure, tumor's margin is obscured by the fissure | 0, 1 | 0-no; 1-yes |
| Pleural attachment | tumor attaches to the pleura other than fissure, tumor's margin is obscured by the pleura | 0, 1 | 0-no; 1-yes |
| | the greatest dimension in lung window | 1, 2, 3, 4, 5 | 1-≤2 cm; 2->2-3 cm; 3->3-5 cm; 4->5-7 cm; 5->7 cm |
| Size | | | |
| Shape | | | |
| Sphericity | roundness | 1, 2, 3, 4, 5 | 1-round; 2, 3, 4, 5-elongated with increasing degrees |
| Lobulation | contours with undulations | 1, 2, 3, 4, 5 | 1-none; 2, 3, 4, 5-lobulated with increasing degrees |
| Concavity | concave cuts | 1, 2, 3, 4, 5 | 1-none; 2, 3, 4, 5-concaved with increasing degrees |
| Irregularity | complex shape | 1, 2, 3, 4, 5 | 1-smooth; 2, 3, 4, 5-irregular with increasing degrees |
| Margin | | | |
| Border definition | well or ill-defined border | 1, 2, 3, 4, 5 | 1-well defined; 2, 3, 4, 5-poorly defined with increasing degrees |
| Spiculation | lines radiating from the margins of the tumor | 1, 2, 3, 4, 5 | 1-none; spiculated with increasing degrees |
| Density | | | |
| Texture | solid or ground-glass opacity | 1, 2, 3, 4, 5 | 1-Nonsolid (pure ground-glass opacity); 2-Partly solid, small extent of solid component; 3-Partly solid, large extent of solid component; 4-solid, with relatively low density; 5-solid |

TABLE 22-continued

Lexicon of CT characteristics for lung adenocarcinoma

| Characteristic | Definition | Scoring | Scoring definition |
|---|---|---|---|
| Air space | including cavity and pseudocavity due to the difficulty to differentiate on CT images | 1, 2, 3, 4, 5 | 1-None; 2, 3, 4, 5-from small to large extent of lucencies |
| Air bronchogram | tubelike or branched air structure within the tumor | 1, 2, 3, 4, 5 | 1-None; 2, 3, 4, 5-from small to large extent of air bronchogram |
| Enhancement heterogeneity | heterogeneity of tumor on contrast-enhanced images | 1, 2, 3, 4, 5 | 1-homogeneous; 2, 3, 4, 5-from mildly to highly heterogeneous |
| Calcification | any patterns of calcification in the tumor | 0, 1 | 0-no; 1-yes |
| Surrounding tissues | | | |
| Pleural retraction | retraction of the pleura towards the tumor | 1, 2, 3, 4, 5 | 1-None; 2, 3, 4, 5-from slight to obvious pleural retraction |
| Vascular convergence | convergence of vessels to the tumor, only applied to the peripheral tumors | 1, 2, 3, 4, 5 | 1-None; 2, 3, 4, 5-from slight to obvious vascular convergence |
| Thickened adjacent bronchovascular bundle | widening of adjacent bronchovascular bundle | 1, 2, 3, 4, 5 | 1-None; 2, 3, 4, 5-from slightly to obviously thickened |
| Emphysema periphery | peripheral emphysema caused by the tumor or preexisting emphysema | 1, 2, 3, 4, 5 | 1-none; 2, 3, 4, 5-from mild to severe emphysema |
| Fibrosis periphery | peripheral fibrosis caused by the tumor or preexisting fibrosis | 1, 2, 3, 4, 5 | 1-none; 2, 3, 4, 5-from mild to severe fibrosis |
| Associated findings | | | |
| Nodules in primary tumor lobe | any nodules suspected malignant or indeterminate | 0, 1 | 0-no; 1-yes |
| Nodules in nontumor lobes | any nodules suspected malignant or indeterminate | 0, 1 | 0-no; 1-yes |
| Lymphadenopathy | thoracic lymph nodes with short axis greater than 1 cm | 0, 1 | 0-no; 1-yes |
| Vascular involvement | vessels narrowed, occluded or encased by the tumor, only applied to the contrast-enhanced images | 0, 1 | 0-no; 1-yes |

TABLE 23

Differences between our descriptors and BI-RADS (Fourth edition for Mammography) for shape and margin

| BI-RADS | Descriptors | Scale |
|---|---|---|
| Shape | | |
| Round | Sphericity | 1 |
| Oval | Sphericity | 2 to 5 |
| Lobular | Lobulation | 3 to 5 |
| Irregular | Irregularity | 2 to 5 |
| | Concavity | 1 to 5 |
| Margin | | |
| Circumscribed (Well-Defined or Sharply-Defined) | Border definition | 1 |
| Microlobulated | Lobulation* | 2 |
| Obscured | Fissure or pleural attachment† | |
| Indistinct (Ill-Defined) | Border definition | 2 to 5 |
| Spiculated | Spiculation | 2 to 5 |

*In shape group
†In space localization group

TABLE 24

Distribution of the CT imaging characteristics among 117 lung cancer patients

| CT characteristic | N | (%) |
|---|---|---|
| Location | | |
| 1 | 35 | (29.9) |
| 2 | 9 | (7.7) |
| 3 | 20 | (17.1) |
| 4 | 37 | (31.6) |
| 5 | 16 | (13.7) |
| Distribution | | |
| 0 | 9 | (7.7) |
| 1 | 108 | (92.3) |
| Fissure attachment | | |
| 0 | 81 | (69.2) |
| 1 | 36 | (30.8) |

TABLE 24-continued

Distribution of the CT imaging characteristics among 117 lung cancer patients

| CT characteristic | N | (%) |
|---|---|---|
| Pleural attachment | | |
| 0 | 82 | (70.1) |
| 1 | 35 | (29.9) |
| Size | | |
| 1 | 29 | (24.8) |
| 2 | 46 | (39.3) |
| 3 | 35 | (29.9) |
| 4 | 7 | (6.0) |
| Sphericity | | |
| 1 | 7 | (6.0) |
| 2 | 18 | (15.4) |
| 3 | 65 | (55.6) |
| 4 | 24 | (20.5) |
| 5 | 3 | (2.6) |
| Lobulation | | |
| 1 | 3 | (2.6) |
| 2 | 34 | (29.1) |
| 3 | 48 | (41.0) |
| 4 | 28 | (23.9) |
| 5 | 4 | (3.4) |
| Concavity | | |
| 1 | 6 | (5.1) |
| 2 | 37 | (31.6) |
| 3 | 38 | (32.5) |
| 4 | 28 | (23.9) |
| 5 | 8 | (6.8) |
| Irregularity | | |
| 2 | 22 | (18.8) |
| 3 | 44 | (37.6) |
| 4 | 34 | (29.1) |
| 5 | 17 | (14.5) |

TABLE 25

| CT characteristic | N | (%) |
|---|---|---|
| Border definition | | |
| 1 | 2 | (1.7) |
| 2 | 50 | (42.7) |
| 3 | 40 | (34.2) |
| 4 | 17 | (14.5) |
| 5 | 8 | (6.8) |
| Spiculation | | |
| 1 | 6 | (5.1) |
| 2 | 46 | (39.3) |
| 3 | 33 | (28.2) |
| 4 | 26 | (22.2) |
| 5 | 6 | (5.1) |
| Texture | | |
| 1 | 3 | (2.6) |
| 2 | 18 | (15.4) |
| 3 | 35 | (29.9) |
| 4 | 30 | (25.6) |
| 5 | 31 | (26.5) |
| Air space | | |
| 1 | 65 | (55.6) |
| 2 | 30 | (25.6) |
| 3 | 16 | (13.7) |
| 4 | 5 | (4.3) |
| 5 | 1 | (0.9) |
| Air bronchogram | | |
| 1 | 75 | (64.1) |
| 2 | 26 | (22.2) |
| 3 | 8 | (6.8) |
| 4 | 6 | (5.1) |
| 5 | 2 | (1.7) |
| Enhancement heterogeneity | | |
| 1 | 2 | (1.7) |
| 2 | 10 | (8.6) |
| 3 | 34 | (29.1) |
| 4 | 28 | (23.9) |
| 5 | 18 | (15.4) |
| N/A | 25 | (21.4) |
| Calcification | | |
| 0 | 111 | (94.9) |
| 1 | 6 | (5.1) |
| Pleural retraction | | |
| 1 | 12 | (10.3) |
| 2 | 34 | (29.1) |
| 3 | 42 | (35.9) |
| 4 | 26 | (22.2) |
| 5 | 3 | (2.6) |
| Vascular convergence | | |
| 1 | 23 | (19.7) |
| 2 | 35 | (29.9) |
| 3 | 22 | (18.8) |
| 4 | 24 | (20.5) |
| 5 | 6 | (5.1) |
| NA | 7 | (6.0) |
| Thickened adjacent bronchovascular bundle | | |
| 1 | 83 | (70.9) |
| 2 | 15 | (12.8) |
| 3 | 17 | (14.5) |
| 4 | 1 | (0.9) |
| 5 | 1 | (0.9) |
| Emphysema periphery | | |
| 1 | 52 | (44.4) |
| 2 | 25 | (21.4) |
| 3 | 28 | (23.9) |
| 4 | 9 | (7.7) |
| 5 | 3 | (2.6) |
| Fibrosis periphery | | |
| 1 | 7 | (6.0) |
| 2 | 27 | (23.1) |
| 3 | 50 | (42.7) |
| 4 | 26 | (22.2) |
| 5 | 7 | (6.0) |
| Nodules in primary tumor lobe | | |
| 0 | 60 | (51.3) |
| 1 | 57 | (48.7) |
| Nodules in non-tumor lobes | | |
| 0 | 45 | (38.5) |
| 1 | 72 | (61.5) |
| Lymphadenopathy | | |
| 0 | 83 | (70.9) |
| 1 | 34 | (29.1) |
| Vascular involvement | | |
| 0 | 33 | (28.2) |
| 1 | 61 | (52.1) |
| N/A | 23 | (19.7) |

TABLE 26

Hazard ratios for the association between the CT characteristics and overall survival

| | Overall mHR (95% CI)[1] | Group 1[3] mHR (95% CI)[1] | Group 2[3] mHR (95% CI)[1] |
|---|---|---|---|
| Main effects | | | |
| Pleural attachment | 3.42 (1.70-6.86) | 5.98 (1.78-20.16) | 2.22 (0.85-5.83) |
| Air bronchogram | 1.48 (0.76-2.91) | 1.11 (0.33-3.73) | 1.47 (0.60-3.61) |
| Lymphadenopathy | 1.88 (0.91-3.87) | 0.44 (0.50-3.84) | 2.90 (1.08-7.80) |
| Final Model[2] | | | |
| Pleural attachment | 3.56 (1.74-7.29) | 5.98 (1.78-20.16) | NI |
| Air bronchogram | NI | NI | NI |
| Lymphadenopathy | 2.00 (0.94-4.25) | NI | 2.90 (1.08-7.80) |

Bolded values indicate a statistically significant result
[1]Adjusted for age, race, gender, smoking status, histological subtype, and stage, where appropriate
[2]The finals were derived from forward stepwise regression modeling with a 0.1 significance level for inclusion into the model. Adjustment factors were forced into the forward stepwise selection model. The features that were not included in the final model were designated as 'NI'
[3]Group 1 are adenocarcinoma tumors showing pure lepidic growth or with lepidic growth as its predominant component; group 2 are adenocarcinoma tumors without a predominantly lepidic component Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for diagnosing tumors in a subject by performing a quantitative analysis of a radiological image, comprising:
    identifying, using a processor, a region of interest (ROI) in the radiological image;
    segmenting the ROI from the radiological image using the processor;
    identifying a tumor object in the segmented ROI using the processor;
    segmenting the tumor object from the segmented ROI using the processor;
    extracting, by the processor, a plurality of quantitative features describing the segmented tumor object; and
    classifying the tumor object based on the extracted quantitative features using the processor, wherein the quantitative features include one or more texture-based features and wherein a total number of quantitative features is greater than approximately 10.

2. The method of claim 1, wherein classifying the tumor object based on the extracted quantitative features further comprises predicting whether the tumor object is a malignant or benign tumor.

3. The method of claim 1, wherein classifying the tumor object based on the extracted quantitative features further comprises using a decision tree algorithm, a nearest neighbor algorithm or a support vector machine.

4. The method of claim 1, wherein each of the texture-based features describes a spatial arrangement of image intensities within the tumor object.

5. The method of claim 1, wherein the texture-based features include at least one of a run-length texture feature, a co-occurrence texture feature, a Laws texture feature, a wavelet texture feature or a histogram texture feature.

6. The method of claim 1, wherein the quantitative features include one or more shape-based features.

7. The method of claim 6, wherein each of the shape-based features describes a location, a geometric shape, a volume, a surface area, a surface-area-to-volume ratio or a compactness of the tumor object.

8. The method of claim 1, wherein a total number of quantitative features is greater than approximately 200.

9. The method of claim 8, wherein a number of texture-based features is greater than approximately 150.

10. The method of claim 1, wherein the ROI is a lung field.

11. The method of claim 1, wherein the radiological image is a low-dose computed tomography (CT) image.

12. A method for diagnosing tumors in a subject by performing a quantitative analysis of a radiological image, comprising:
    Identifying, using a processor, a region of interest (ROI) in the radiological image;
    segmenting the ROI from the radiological image using the processor;
    identifying a tumor object in the segmented ROI using the processor;
    segmenting the tumor object from the segmented ROI using the processor;
    extracting, using the processor, a plurality of quantitative features describing the segmented tumor object;
    reducing, by the processor, the extracted plurality of quantitative features to a subset of extracted quantitative features; and
    classifying, by the processor, the tumor object based on the subset of extracted quantitative features, wherein the quantitative features include one or more texture-based features.

13. The method of claim 12, wherein the subset of extracted quantitative features includes one or more quantitative features that are predictive of the classification of the tumor object.

14. The method of claim 13, further comprising determining the one or more quantitative features that are predictive of the classification of the tumor object using at least one of a Recursive Elimination of Features (Relief-F) algorithm, a Correlation-Based Feature Subset Selection for Machine Learning (CFS) algorithm or a Relief-F with Correlation Detection algorithm.

15. The method of claim 12, wherein the subset of extracted quantitative features includes one or more non-redundant quantitative features having adequate reproducibility and dynamic range.

16. The method of claim 15, wherein reducing the extracted quantitative features to a subset of extracted quantitative features further comprises eliminating one or more of the extracted quantitative features having a reproducibility metric between a baseline radiological image and a subsequent radiological image less than a predetermined reproducibility value, the subsequent radiological image being captured a fixed period of time after the baseline radiological image was captured.

17. The method of claim 16, wherein the reproducibility metric is a concordance correlation coefficient.

18. The method of claim 16, wherein the predetermined reproducibility value is less than 0.90.

19. The method of claim 16, wherein reducing the extracted quantitative features to a subset of extracted quantitative features further comprises eliminating one or more of the extracted quantitative features having a dynamic range less than a predetermined dynamic range value.

20. The method of claim 16, wherein reducing the extracted quantitative features to a subset of extracted quantitative features further comprises eliminating one or more of the extracted quantitative features that are redundant quantitative features.

21. The method of claim 20, further comprising calculating a coefficient of determination ($R^2_{Bet}$) between at least two quantitative features, wherein the $R^2_{Bet}$ of each of the redundant quantitative features is less than a predetermined redundancy value.

22. The method of claim 21, wherein predetermined redundancy value is 0.95.

* * * * *